(12) United States Patent
Cherkassky et al.

(10) Patent No.: US 11,155,851 B2
(45) Date of Patent: Oct. 26, 2021

(54) COMPOUNDS AND METHODS RELATING TO LYSOSOMAL STORAGE DISORDERS

(71) Applicants: University of Washington through its Center of Commercialization, Seattle, WA (US); PerkinElmer Health Sciences, Inc., Waltham, MA (US)

(72) Inventors: Alexander Cherkassky, Wayland, MA (US); Jason Coumoyer, Jamaica Plain, MA (US); Michael Gelb, Seattle, WA (US)

(73) Assignees: University of Washington through its Center for Commercialization, Seattle, WA (US); PerkinElmer Health Sciences, Inc., Waltham, MA (US)

( * ) Notice: Subject to any disclaimer, the term of this patent is extended or adjusted under 35 U.S.C. 154(b) by 942 days.

(21) Appl. No.: 15/188,239

(22) Filed: Jun. 21, 2016

(65) Prior Publication Data

US 2016/0298169 A1   Oct. 13, 2016

Related U.S. Application Data

(62) Division of application No. 14/215,885, filed on Mar. 17, 2014, now abandoned.

(60) Provisional application No. 61/789,985, filed on Mar. 15, 2013.

(51) Int. Cl.
*C12Q 1/34* (2006.01)
*C07C 233/18* (2006.01)
*C07H 15/10* (2006.01)

(52) U.S. Cl.
CPC .............. *C12Q 1/34* (2013.01); *C07C 233/18* (2013.01); *C07H 15/10* (2013.01); *G01N 2333/924* (2013.01)

(58) Field of Classification Search
CPC ........ C12Q 1/34; C07C 233/18; C07H 15/10; G01N 2333/924
See application file for complete search history.

(56) References Cited

U.S. PATENT DOCUMENTS

| | | | |
|---|---|---|---|
| 4,968,785 A | 11/1990 | Moser et al. | |
| 5,138,043 A | 8/1992 | Polovsky et al. | |
| 5,384,334 A | 1/1995 | Polovsky et al. | |
| 6,797,281 B1 | 9/2004 | Pisano et al. | |
| 6,852,544 B2 | 2/2005 | Aebersold et al. | |
| 8,173,784 B2 | 5/2012 | Cerda et al. | |
| 8,268,865 B2 | 9/2012 | Glinka et al. | |
| 8,791,246 B2 | 7/2014 | Cerda et al. | |
| 2005/0232929 A1 | 10/2005 | Kadkhodayan et al. | |
| 2006/0052316 A1 | 3/2006 | Porcelli | |
| 2008/0248512 A1* | 10/2008 | Zhang | A61K 31/164 435/18 |
| 2009/0068634 A1 | 3/2009 | Cerda | |

FOREIGN PATENT DOCUMENTS

| | | |
|---|---|---|
| EP | 0631779 A1 | 1/1995 |
| JP | 8145948 A | 6/1996 |
| JP | 11116589 A | 4/1999 |
| JP | 2006524040 A | 10/2006 |
| JP | 2007532882 A | 11/2007 |
| JP | 4364197 B2 | 11/2009 |
| WO | WO-200127074 A1 | 4/2001 |
| WO | WO-200177674 A2 | 10/2001 |
| WO | WO-2004072238 A2 | 8/2004 |
| WO | WO-2007013601 A1 | 2/2007 |
| WO | WO-2007/106816 A2 | 9/2007 |
| WO | 2008033427 A2 | 3/2008 |
| WO | WO-2008033427 A2 | 3/2008 |
| WO | WO-2010015816 A2 | 2/2010 |

OTHER PUBLICATIONS

Osiecki-Newman et al., Biochimica et Biophysica Acta, vol. 915, pp. 87-100 (1987).*
Chapman, Jacqueline V., et al., "P-glycoprotein antagonists confer synergistic sensitivity to short-chain ceramide in human multidrug resistance cancer cells," *Experimental Cell Research*, vol. 317, No. 12, Jul. 1, 2011 pp. 1736-1745.
Kasper, David C. et al., "The application of multiplexed, multi-dimensional ultra-high-performance liquid chromatography/tandem mass spectrometry to the high-throughput screening of lysosomal storage disorders in newborn dried bloodspots," *Rapid Communications in Mass Spectrometry*, vol. 24, No. 7, Apr. 15, 2010, pp. 986-994.
CN Office Action dated Dec. 22, 2017 for corresponding CN application No. 201480027876.3.
Li, Y. et al., "Direct Multiplex Assay of Lysosomal Enzymes in Dried Blood Spots for Newborn Screening," Clinical Chemistry, 50:10 1785-1796 (2004).
Gelb, Michael H., "Direct multiplex assay of enzymes in dried blood spots by tandem mass spectrometry for the newborn screening of lysosomal storage disorders," J Inherit Metab Dis, 29:397-404 (2006).
Rozaklis et al.; Determination of Oligosaccharides in Pompe Disease by Electrospray Ionization Tandem Mass Spectrometry; Clinical Chemistry, vol. 48, No. 1, 2002; pp. 131-139.

(Continued)

*Primary Examiner* — Sharmila G Landau
*Assistant Examiner* — Paul D. Pyla
(74) *Attorney, Agent, or Firm* — Dinsmore & Shorn LLP; Weston R. Gould

(57) ABSTRACT

Methods are provided for detecting enzymatic activity of various lysosomal storage enzymes using substrates that include: a sugar moiety; a linker moiety allowing the conjugation of sugar moiety with the remaining structure of the substrate; and two or more fatty acid chains or derivatives thereof at least one of which is sufficiently structured to provide improved solubility in aqueous or organic solvent systems. Also provided are internal standards, and inhibitors for use in detecting or reducing enzymatic activity using the inventive substrates.

11 Claims, 7 Drawing Sheets

(56) References Cited

OTHER PUBLICATIONS

Umapathysivam et al., Determination of Acid Alpha-Glucosidase Protein: Evaluation as a Screening Marker for Pompe Disease and Other Lysosomal Storage Disorders; Clinical Chemistry, vol. 46, No. 9, 2000; pp. 1318-1325.

Umapathysivam et al.; Determination of Acid Alpha-Glucosidase Activity in Blood Spots as a Diagnostic Test for Pome Disease, Clinical Chemistry; vol. 47; No. 8, 2001; pp. 1378-1383.

Okumiya T et al.; A New Diagnostic Assay for Glycogen Storage Disease Type II in Mixed Leukocytes; Molecular Genetics and Metabolism; Academic Press; San Diego, CA, vol. 88; No. 1; Dec. 2005; pp. 22-28.

T.J.P. Maven et al., Cationic Derivatization of Oligosaccharides with Girard's I Reagent for Improved Performance in Matrix-assisted Laser Desorption/Ionization and Electrospray Mass Spectrometry; Rapid Communications in Mass Spectrometry, vol. 10, pp. 829-834; (1996).

Deschavanne et al., J Biol Chem, 253(3), p. 833-837 (1978).

Czjzek et al., PNAS, 2000, 97(25), p. 13555-13560.

Erickson et al., J. Lipid Res., 1973, 14, p. 133-137.

Halling et al.; Understanding Enzyme Action on Immobilised Substrates; vol. 16, No. 4,; Aug. 1, 2005; pp. 385-392.

Gelman, Benjamin B., et al.; Mononuclear Phagocyte Hdrolytic Enzyme Activity Associated with Cerebral HIV-1 Infection; American Journal of Pathology, vol. 151, No. 5, Nov. 1997; pp. 1437-1446.

Demartino, George N. et al.; Thyroid hormones control lysosomal enzyme activities in liver and skeletal muscle; Proc. Natl. Acad. Sci. USA, vol. 75, No. 3; pp. 1369-1373; Mar. 1978; Cell Biology.

ELISA—Introduction to Antibodies; Introduction to Antibodies-Enzyme-Linked Immunosorbent Assay (ELISA); <http://www.chemicon.com>; pp. 1-6 (reprinted from website Jun. 1, 2007).

Gibbs, J. Immobilization Principles—Selecting the Surface; ELISA Technical Bulletin—No. 1; Corning Life Sciences, pp. 1-8 (2007). Corning Assay Surfaces Selection Guide; <http://www.corning.com>; pp. 1-3 (Jul. 2001).

Cartine and Acylcarntines; Carntine and acylcarntines: structure, occurrence, biology and analysis, www.lipidlibrary.co.uk <http://www.lipidlibrary.co.uk>; pp. 1-2 (2007).

Cerezyme; pp. 1-2 (Dec. 3, 2007).

Boot, Rolf G. et al.; Identification of the Non-lysosomal Glucosylceramidase as B-Glucosidase 2; Journal of Biological Chemistry; Jan. 12, 2007; vol. 282, No. 2; pp. 1305-1312.

Biovision; Glucose Assay Kit; BioVision Research Products, pp. 1 of 1 (Apr. 2006).

Alexa Fluor Succinimidyl Esters; Invitrogen; Molecular Probes, Revised: Feb. 6, 2007, pp. 1-5.

Amine-Reactive Probes; Invitrogen, Molecular Probes; Revised: Feb. 6, 2007; pp. 1-9.

Minimum Recommendations for Monitoring Patients with Non-Neuronopathic (Type 1) Gaucher Disease; Gaucher Registry; www.gaucherregistry.com; p. 1 of 1 (Mar. 2003).

Amplex® Red Galactose/Galactose Oxidase Kit (A22179), Molecular Probes Production Information, Amplex® Red Galactose/Galactose Oxidase Kit, Revised: Oct. 1, 2004, pp. 1-4.

Amplex® Red Glucose/Glocose Oxidase Assay Kit; Invitrogen Molecular Probes, Revised: May 22, 2006; pp. 1-7.

Leonard, Renaud et al.; The *Drosophila* fused lobes Gene Encodes an N-Acetylplucosaminidase involved in N-Glycan Processing; The Journal of Biological Chemistry; vol. 281, No. 8 (2006) pp. 4867-4875.

Lundquist, Ingmar et al.; Islet Acid Glucan-1, 4-x-Glucosidease: A Putative Key Enzyme in Nutrient-Stimulated Insulin Secretion; Endocrinology, vol. 137; No. 4 (1996) pp. 1219-1225.

Ramsay, Steven L. et al.; Determination of oligosaccharides and glycolipids in amniotic fluid by electrospray ionization tandem mass spectrometry; in utero indicators of lysosomal storage diseases; Molecular Genetics and Metabolism 83 (2004) pp. 231-238; www.elsevier.com <http://www.elsevier.com>.

Rosenberg, M. et al., "Immunosurveillance of Algucerase Enzyme Therapy for Gaucher Patients; Induction of Humoral Tolerance in Seroconverted Patients After Repeat Administration; Phagocytes Blood", vol. 93; No. 6; (Mar. 15); 1999; pp. 2081-2088.

Zhou, Mingjie et al; Two Fluorometric Approaches to the Measurement of Dextranase Activity; Analytical Biochemistry 260, 257-259; (1998); Article No. AB982733.

Daniels, Lydia B. et al., "A revised fluorometric assay for Gaucher's disease using conduritol-β-epoxide with liver as the source of β-glucosidase," Clinca Chimica Acta, 106 (1980) 155-163.

Suzuki, Kunihiko et al., "Globoid Cell Leucodystrophy (Krabbe's Disease): Deficiency of Galactocerebroside β-Galactosidase," Proceedings of the National Academy of Sciences, vol. 66, No. 2, pp. 302-309, Jun. 1970.

Von Deyn, Wolfgang, et al., "1-Alkoxyamino-1-deoxy alditols, useful u.v.-absorbing derivatives of neutral and acidic oligosaccharides," Carbolydrate Research, 201 (1990) 135-144.

Donald, A.S.R., "Separation of hexosamines, hexosaminitols and hexosamine-containing diand trisaccharides on an amino acid analyser," Journal of Chromatography, 134 (1977) 199-203.

International Search Report and Written Opinion for co-pending PCT Application No. PCT/US2014/030183 dated Aug. 28, 2014.

Schulze, Heike et al., "Lysomal Lipid Storage Diseases," Cold Spring Harbor Perspectives in Biology, vol. 3, No. 6, pp. 1-14, Apr. 18, 2011.

Chang et al., Journal of the American Chemical Society—2002, 124(9) pp. 1856-1857.

Karen Osiecki-Newman et al, Human Acid ß-glucosidase: Use of Inhibitors, Alternative Substrates and Amphiphiles to Investigate the Properties of the Normal and Gaucher Disease Active Sites; Biochimica et Biophysica Acta 915 (1987) 87-100.

David C. Kasper et al, The Application of Multiplexed, Multi-Dimensional Ultra-High-Performance Liquid Chromatography/Tandem Mass Spectrometry to the High-Throughput Screening of Lysosomal Storage Disorders in Newborn Dried Bloodspots; Rapid Communication in Mass Spectrometry, 2010; 24: 986-994.

Ghafourifar, P. et al., Ceramide Induces Cytochrome c Release from Isolated Mitochondria, 274(10): 6080-6084, Mar. 5, 1999.

\* cited by examiner

COMPOUNDS AND METHODS RELATING TO LYSOSOMAL STORAGE DISORDERS

CROSS REFERENCE TO RELATED APPLICATIONS

This application is a divisional of U.S. patent application Ser. No. 14/215,885 filed Mar. 17, 2014, and which depends from and claims priority to U.S. Provisional Application No. 61/789,985 filed Mar. 15, 2013, the entire contents of each of which are incorporated herein by reference.

STATEMENT OF GOVERNMENT SUPPORT

This invention was made with government support under grant no. DK067859, awarded by the National Institutes of Health. The government has certain rights in the invention.

FIELD

The present description relates to analytical reagents for detecting enzymatic activity for detecting lysosomal enzyme activity.

BACKGROUND

Lysosomal storage disorders are a group of inherited disorders characterized by deficiencies in specific enzymes in the body, which results in the body's inability to break down metabolic substances. As an example, Fabry disease is a lysosomal storage disorder seen in one out of every 40,000 people. It is caused by a deficiency in the enzyme alpha-galactosidase which results in the body's inability to break down specific fatty substances called globotriaosylceramides. A second example is Gaucher disease, a lysosomal storage disorder caused by an inability to break down fatty substances or lipids called glucosylceramides (also called glucocerebrosides). Individuals with Gaucher disease do not make glucocerebrosidase, an enzyme needed to break down these fatty substances. These fatty substances then accumulate in cells of the liver, spleen, and bone marrow. A third example is Pompe disease, a lysosomal storage disorder caused by a deficiency in the enzyme acid alpha-glucosidase, which is needed to break down certain sugars called glycogen. When the enzyme acid alpha-glucosidase is missing, glycogen accumulates in various tissues and organs in the body.

Lysosomal storage disorders are, for the most part, childhood disorders although some manifest in adulthood. In most of them, patients are normal at birth and have progressive neurological deterioration beginning at some later time. The clinical phenotype depends on the type and severity of the biochemical defect. Some of these lysosomal disorders, such as Pompe disease and Krabbe disease, manifest primarily in infancy. There have been ongoing efforts in developing methods to detect such disorders before the onset of clinical symptoms so that therapeutic interventions can be initiated.

Over the past decade laboratories that test for metabolic disorders have introduced tandem mass spectrometry into their newborn screening programs. Tandem mass spectrometry continues to gain popularity in the clinic because this technology allows for assay of many metabolites in a single sample. For example, this technology has been implemented as a routine clinical practice for the detection of hereditary metabolic disorders in newborns using dry blood spot samples. Although lysosomal enzyme activities can be quantified using tandem mass spectrometry, published assay methods have been somewhat difficult to adapt to a clinical setting due to solubility issues and the need for incorporation of an external standard.

Thus, there is a continuing need for improving the methods and compositions for detecting lysosomal disorders.

SUMMARY

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

Improved compositions and processes for detecting enzymatic reactions using detection systems such as mass spectrometry are provided. These compositions provide for improved solubility in aqueous solvent systems and/or improved reactivity with a target enzyme thereby improving assay efficiency, reproducibility, and accuracy.

The invention provides chemical compounds useful for assessing the level of lysosomal enzyme activity in a sample. Testing of lysosomal enzyme activity is useful, for example, when screening for metabolic disorders in newborns as well as when assessing an individual having a medical condition affecting enzyme activity or one undergoing a medical treatment such as enzyme replacement therapy, gene therapy, or bone marrow transplantation. The chemical compounds described herein include substrates for target enzymes and related molecules useful as controls or standards in enzyme assays.

It is one object of the invention to provide substrates suitable for detecting the activity of an enzyme, illustratively an enzyme the deficiency of which leads to a lysosomal storage disorder. Substrate are provided that have the general formula:

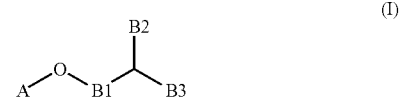

(I)

where A is a monosaccharide or a disaccharide; B1 is: a $C_1$-$C_{20}$ alkyl; a heteroatom containing $C_1$-$C_{20}$ alkyl, $C_2$-$C_{20}$ alkenyl; a heteroatom containing $C_2$-$C_{20}$ alkenyl, a substituted or unsubstituted $C_6$-$C_{20}$ aryl; B2 is: a $C_2$-$C_7$ urethane; a $C_2$-$C_7$ amido, a $C_2$-$C_7$ ester, a $C_2$-$C_7$ uriedo; a $C_2$-$C_7$ carbamato; a $C_2$-$C_7$ carbonyl; a $C_1$-$C_7$ alkyl; a heteroatom containing $C_1$-$C_7$ alkyl; a $C_1$-$C_7$ alkyl having a substituent of N, O, or S; a $C_2$-$C_7$ alkenyl; a heteroatom containing $C_2$-$C_7$ alkenyl; a $C_2$-$C_7$ alkenyl having a substituent of N, O, or S; and B3 is: a $C_1$-$C_{20}$ alkyl, a heteroatom containing $C_1$-$C_{20}$ alkyl; $C_1$-$C_{20}$ alkyl having a substituent of N, O, or S; $C_4$-$C_{20}$ ether; $C_1$-$C_{20}$ ester, $C_1$-$C_{20}$ alkenyl; a heteroatom containing $C_1$-$C_{20}$ alkenyl; $C_2$-$C_{20}$ alkenyl having a substituent of N, O, or S; $C_1$-$C_{20}$ alkynl; a heteroatom containing $C_1$-$C_{20}$ alkynl; $C_2$-$C_{20}$ alkynl having a substituent of N, O, or S $C_6$-$C_{20}$ aryl; and $C_6$-$C_{20}$ heterocyclic containing a heteroatom of N, O or S. A substituent of N, O, or S is independently optionally a hydroxyl, an amino, a thiol, ether, thioether, or secondary amine. In some embodiments, A is an aldohexose or a ketohexose, optionally linked through and α or 3 glycosidic bond to the remainder of the molecule. Optionally, A is a D-glucose or a D-galactose. A B1 moiety is optionally a methylene or $C_2$ alkyl group. A B2 moiety is optionally a $C_2$-$C_7$ amido. A B3 moiety is optionally a $C_2$-$C_{20}$ alkenyl-having a substituent of N, O, or S. In some embodiments, a substrate includes an A that is D-glucose or a D-galactose, A B1 that is a methylene, a B1 that is a $C_2$-$C_7$ amido, and B3 that is a $C_{13}$-$C_{20}$ alkenyl having a substituent of O present as a hydroxyl.

Also provided are compounds of the general Formula II,

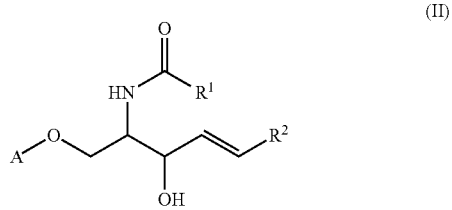

(II)

that is similarly useful as a substrate for detection of lysosomal storage disorder. According to Formula II A is an aldohexose or ketohexose; $R^1$ is a $C_1$-$C_6$ alkyl or a $C_2$-$C_{20}$ alkenyl; and $R^2$ is a $C_1$-$C_{20}$ alkyl, a $C_1$-$C_{20}$ alkyl having a substituent of N, O, or S, a $C_1$-$C_{20}$ alkenyl, or a $C_1$-$C_{20}$ alkenyl having a substituent of N, O or S. It is appreciated that $R^1$ or $R^2$ could be a $C_1$-$C_{20}$ alkynl optionally containing a substitution of N, O, or S, or a substituent of N, O, or S. In some embodiments, the substrate of formula II includes A as a D-glucose or D-galactose, $R^1$ as a $C_4$-$C_6$ alkyl, and $R^2$ is a $C_{13}$-$C_{20}$ alkyl, a $C_{13}$-$C_{20}$ alkyl having a substituent of N, O, or S, a $C_{13}$-$C_{20}$ alkenyl, or a $C_{13}$-$C_{20}$ alkenyl having a substituent of N, O or S. Optionally, $R^2$ is a $C_{13}$ alkyl.

Also provided are substrates suitable for detecting the presence or absence of a lysosomal storage disorder or simply for detecting the presence or absence of an enzyme that includes the structure of formula III:

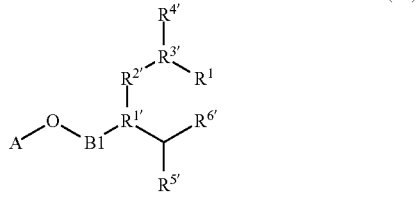

(III)

where A is a monosaccharide or a disaccharide; B1 is: a $C_1$-$C_{20}$ alkyl; a heteroatom containing $C_1$-$C_{20}$ alkyl, $C_2$-$C_{20}$ alkenyl; a heteroatom containing $C_2$-$C_{20}$ alkenyl; and a substituted or unsubstituted $C_6$-$C_{20}$ aryl; $R^{1'}$ is a substituted or unsubstituted C, or N; $R^{2'}$ is a substituted or unsubstituted C, a substituted or unsubstituted N, O, or S; $R^{3'}$ is a substituted or unsubstituted C, N, or O; $R^{4'}$ is a nullity, a substituted or unsubstituted $C_1$-$C_2$, O, or S; $R^1$ is: a $C_1$-$C_6$ alkyl; a heteroatom containing $C_1$-$C_7$ alkyl: a $C_1$-$C_7$ alkyl having a substituent of N, O, or S; a $C_2$-$C_7$ alkenyl; a heteroatom containing $C_2$—C alkenyl; a $C_2$-$C_7$ alkenyl having a substituent of N, O, or S; $R^{5'}$ is a nullity, a substituted or unsubstituted $C_1$-$C_2$; O, or S; and $R^{6'}$ is a $C_1$-$C_{20}$ alkyl, a heteroatom containing $C_1$-$C_{20}$ alkyl; $C_1$-$C_{20}$ alkyl having a substituent of N, O, or S; $C_4$-$C_{20}$ ether; $C_1$-$C_{20}$ ester; $C_1$-$C_{20}$ alkenyl; a heteroatom containing $C_1$-$C_{20}$ alkenyl; $C_2$-$C_{20}$ alkenyl having a substituent of N, O, or S; $C_6$-$C_{20}$ aryl; and $C_6$-$C_{20}$ heterocyclic containing a heteroatom of N, O or S. A is optionally an aldohexose or a ketohexose, optionally linked through and α or β glycosidic bond to the remainder of the molecule. Optionally, A is a D-glucose or a D-galactose. In some embodiments, a substrate according to formula III is:

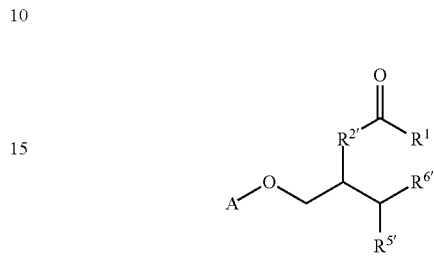

where $R^{2'}$ is a substituted or unsubstituted C or a substituted or unsubstituted N;

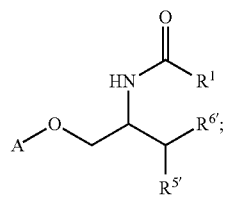

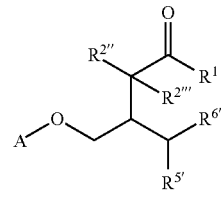

where $R^{2''}$ is a H or a methyl and $R^{2'''}$ is a H or a methyl; or

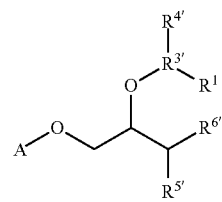

where $R^{3'}$ is a substituted or unsubstituted C; and $R^{4'}$ is a nullity, a substituted or unsubstituted $C_1$-$C_2$, O, or S.

It is appreciated that in any of the above or otherwise included substrates of the invention, A is optionally an aldohexose or a ketohexose, optionally linked through and α or β glycosidic bond to the remainder of the molecule. Optionally, A is a D-glucose or a D-galactose.

In some embodiments, a substrate according to Formula III includes:

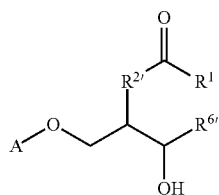

where $R^{2'}$ is a substituted or unsubstituted C or a substituted or unsubstituted N; and $R^{6'}$ is a $C_1$-$C_{20}$ alkyl, a heteroatom containing $C_1$-$C_{20}$ alkyl; $C_1$-$C_{20}$ alkyl having a substituent of N, O, or S; $C_4$-$C_{20}$ ether; $C_1$-$C_{20}$ ester; $C_1$-$C_{20}$ alkenyl; a heteroatom containing $C_1$-$C_{20}$ alkenyl; $C_2$-$C_{20}$ alkenyl having a substituent of N, O, or S; $C_6$-$C_{20}$ aryl; and $C_6$-$C_{20}$ heterocyclic containing a heteroatom of N, O or S;

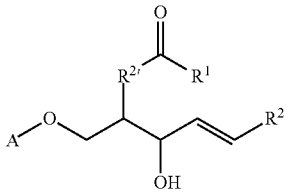

where $R^{2'}$ is a substituted or unsubstituted C or a substituted or unsubstituted N; $R^2$ is a $C_{13}$-$C_{20}$ alkyl, a heteroatom containing $C_{13}$-$C_{20}$ alkyl, a $C_{13}$-$C_{20}$ alkyl having a substituent of N, O, or S; a $C_{13}$-$C_{20}$ alkenyl, a heteroatom containing $C_{13}$-$C_{20}$ alkenyl; or a $C_{13}$-$C_{20}$ alkenyl having a substituent of N, O, or S; or

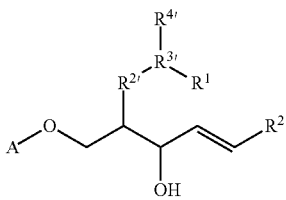

where $R^2$ is a $C_{13}$-$C_{20}$ alkyl, a heteroatom containing $C_{13}$-$C_{20}$ alkyl, a $C_{13}$-$C_{20}$ alkyl having a substituent of N, O, or S; a $C_{13}$-$C_{20}$ alkenyl, a heteroatom containing $C_{13}$-$C_{20}$ alkenyl; or a $C_{13}$-$C_{20}$ alkenyl having a substituent of N, O, or S. In any of the above or otherwise included substrates of the invention, A is optionally an aldohexose or a ketohexose, optionally linked through and α or β glycosidic bond to the remainder of the molecule. Optionally, A is a D-glucose or a D-galactose.

Also provided are substrates including:

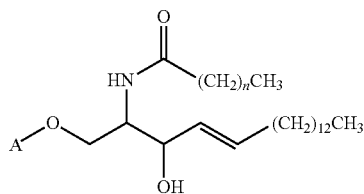

where n is 0, 1, 2, 3, 4, or 5. A is optionally an aldohexose or a ketohexose, optionally linked through and α or β glycosidic bond to the remainder of the molecule. Optionally, A is a D-glucose or a D-galactose.

Any of the substrates of the invention optionally include a stable secondary prevalence isotope of an element or other label. In some embodiments stable secondary prevalence isotope in each occurrence is selected from the group consisting of $^2$H, $^{13}$C, $^{15}$N, $^{17}$O, $^{18}$O, $^{31}$P or $^{34}$S.

It is another object of the invention to provide molecules that can be used as inhibitors of enzyme function, as internal standards for methods of detecting enzyme activity, or as therapeutics. Such molecules optionally include the structure of formula V:

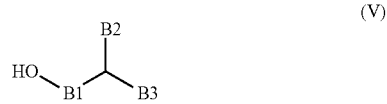

(V)

where B1 is selected from the group consisting of: a $C_1$-$C_{20}$ alkyl; a heteroatom containing $C_1$-$C_{20}$ alkyl, $C_2$-$C_{20}$ alkenyl; a heteroatom containing $C_2$-$C_{20}$ alkenyl, a substituted or unsubstituted $C_6$-$C_{20}$ aryl; B2 is selected from the group consisting of: a $C_2$-$C_7$ urethane; a $C_2$-$C_7$ amido, a $C_2$-$C_7$ ester, a $C_2$-$C_7$ uriedo; a $C_2$-$C_7$ carbamato; a $C_2$-$C_7$ carbonyl; a $C_1$-$C_7$ alkyl; a heteroatom containing $C_1$-$C_7$ alkyl; a $C_1$-$C_7$ alkyl having a substituent of N, O, or S; a $C_2$-$C_7$ alkenyl; a heteroatom containing $C_2$-$C_7$ alkenyl; a $C_2$-$C_7$ alkenyl having a substituent of N, O, or S; and B3 is selected from the group consisting of: a $C_1$-$C_{20}$ alkyl, a heteroatom containing $C_1$-$C_{20}$ alkyl; $C_1$-$C_{20}$ alkyl having a substituent of N, O, or S; $C_4$-$C_{20}$ ether; $C_1$-$C_{20}$ ester, $C_1$-$C_{20}$ alkenyl; a heteroatom containing $C_1$-$C_{20}$ alkenyl; $C_2$-$C_{20}$ alkenyl having a substituent of N, O, or S; $C_1$-$C_{20}$ alkynl; a heteroatom containing $C_1$-$C_{20}$ alkynl; $C_2$-$C_{20}$ alkynl having a substituent of N, O, or S $C_6$-$C_{20}$ aryl; and $C_6$-$C_{20}$ heterocyclic containing a heteroatom of N, O or S. In some embodiments B1 is a methylene. Optionally, B2 is a $C_2$-$C_7$ amido. Optionally, B3 is a $C_2$-$C_{20}$ alkenyl having a substituent of N, O, or S. In some embodiments, B1 is a methylene, B2 is a $C_2$-$C_7$ amido, and B3 is a $C_{13}$-$C_{20}$ alkenyl having a substituent of O present as a hydroxyl.

Any of the molecules of the invention optionally include a stable secondary prevalence isotope of an element or other label. In some embodiments stable secondary prevalence isotope in each occurrence is selected from the group consisting of $^2$H, $^{13}$C, $^{15}$N, $^{17}$O, $^{18}$O, $^{31}$P or $^{34}$S.

Also provided are methods for the detection of the presence, absence, or level of an enzyme, for the detection of the presence or absence of an enzyme deficiency in a subject. An enzyme is optionally an enzyme for which a deficiency in the enzyme leads to a lysosomal storage disorder. Use of the compositions of Formulas I-VI in a method for the detection of the presence, absence, or level of an enzyme allows improved confidence in assay results from the improved solubility of the enzymes in aqueous solvent systems. A method for detecting enzymatic activity includes contacting a sample containing a target enzyme with any of the substrates described herein or their equivalents, under conditions wherein the target enzyme is capable of acting on the substrate to produce an enzymatic product; and detecting the enzymatic product. Optionally, the said target enzyme is acid β-glucocerebrosidase and said substrate of is of formula I wherein said B2 is a $C_2$-$C_7$ amido, and B3 is a $C_2$-$C_{20}$ alkenyl having a substituent of N, O, or S. Optionally, the target enzyme is acid galactocerebroside β-galactosidase or acid-β-glucocerebrosidase and said wherein the B2 is a $C_2$-$C_7$ amido, and B3 is a $C_{13}$-$C_{20}$ having a substituent of O present as a hydroxyl.

Optionally, a substrate for use in a method of detecting enzyme activity is the substrate of any one or more of compound 1 through 80, optionally 1 or 7, or any combination thereof. Optionally, a method includes adding an internal standard to the reaction solution during or following the step of contacting. Such an internal standard is optionally any standard of compositions 81-86.

The step of detecting is optionally by mass spectrometry, optionally by multiple reaction monitoring such as in MS/MS. The step of detecting is optionally by immunoassay, HPLC, mass spectrometry, or other suitable method for detecting molecules with a molecular weight less than 1000 Daltons.

DETAILED DESCRIPTION

Figure 1A:
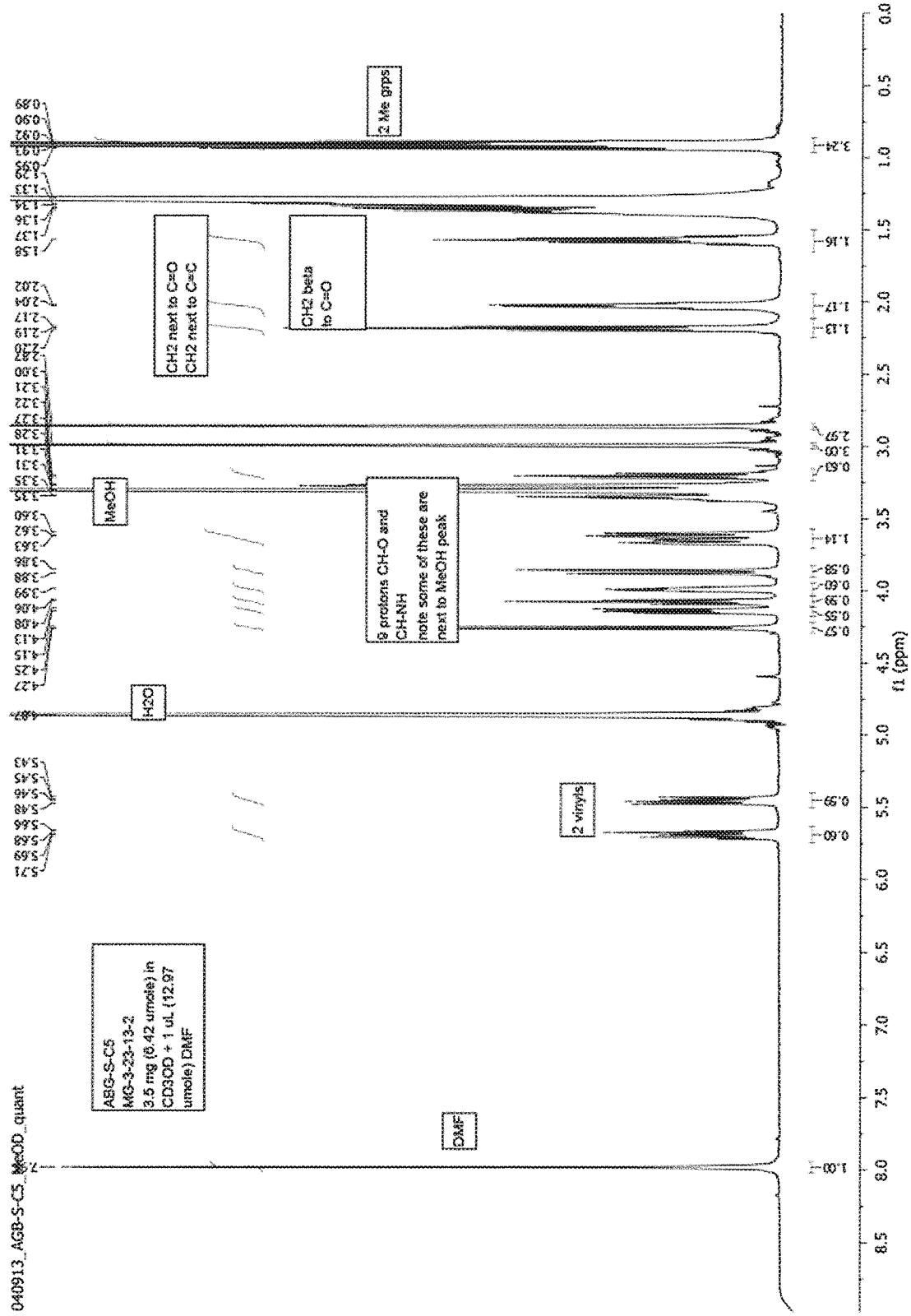
FIG. 1A illustrates NMR analysis of a substrate according to one embodiment.

The following description of particular embodiment(s) is merely exemplary in nature and is in no way intended to limit the scope of the invention, its application, or uses, which may, of course, vary. The compositions or processes are described with relation to the non-limiting definitions and terminology included herein. These definitions and terminology are not designed to function as a limitation on the scope or practice of the invention but are presented for illustrative and descriptive purposes only. While the processes or compositions are described as an order of individual steps or using specific materials, it is appreciated that steps or materials may be interchangeable such that the description of the invention may include multiple parts or steps arranged in many ways as is readily appreciated by one of skill in the art. As such, it is appreciated that various elements of the following compositions are optionally substituted for one another such as any A element is interchangeable with any other A element, any B1 element is substitutable with any other B1 element, any B2 element is substitutable with any other B2 element; any B3 element is substitutable with any other B3 element, any $R^1$ element is substitutable with any other $R^1$ element, any $R^2$ element is substitutable with any other $R^2$ element, any $R^{1'}$ element is substitutable with any other $R^{1'}$ element, any $R^{2'}$ element is substitutable with any other $R^{2'}$ element, any $R^{3'}$ element is substitutable with any other $R^{3'}$ element, any $R^{4'}$ element is substitutable with any other $R^{4'}$ element, any $R^{5'}$ element is substitutable with any other $R^{5'}$ element, or any $R^{6'}$ element is substitutable with any other $R^{6'}$ element. It is appreciated that all combinations of A, B1, B2, B3, $R^1$, $R^2$, $R^{1'}$, $R^{2'}$, $R^{3'}$, $R^{4'}$, $R^{5'}$, or $R^{6'}$ are included herein as is readily appreciated by one of ordinary skill in the art.

The terminology used herein is for the purpose of describing particular embodiments only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. The term "or a combination thereof" means a combination including at least one of the foregoing elements.

Unless otherwise defined, all terms (including technical and scientific terms) used herein have the same meaning as commonly understood by one of ordinary skill in the art to which this disclosure belongs. It will be further understood that terms such as those defined in commonly used dictionaries, should be interpreted as having a meaning that is consistent with their meaning in the context of the relevant art and the present disclosure, and will not be interpreted in an idealized or overly formal sense unless expressly so defined herein.

The compositions provided have utility as analytical reagents for detecting hydrolase enzyme activity, such as lysosomal enzyme activities associated with lysosomal storage disorders. Through the application of enzyme substrates and related compounds useful as experimental controls or standards that are much more readily dissolvable in solutions adaptable for analytical methods such as mass spectrometry, HPLC and immunoassay than previously identified compositions, detecting enzyme activities associated with lysosomal storage disorders is more practical and less cumbersome.

The compositions relate to substrates that are targets for lysosomal enzymes optionally including: acid β-glucocerebrosidase (ABG), galactocerebroside β-galactosidase (GALC). The action of these enzymes over the substrates is used to measure the corresponding enzyme activities in a sample, and thus these substrates may be used to detect the following lysosomal storage disorders: Gaucher (ABG); and Krabbe (GALC).

A substrate has the general formula

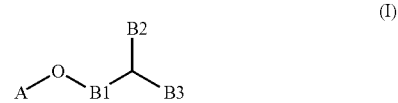

(I)

where A is a monosaccharide or a disaccharide; B1 is: a $C_1$-$C_{20}$ alkyl; a heteroatom containing $C_1$-$C_{20}$ alkyl, $C_2$-$C_{20}$ alkenyl; a heteroatom containing $C_2$-$C_{20}$ alkenyl, a substituted or unsubstituted $C_6$-$C_{20}$ aryl; B2 is: a $C_2$-$C_7$ urethane; a $C_2$-$C_7$ amido, a $C_2$-$C_7$ ester, a $C_2$-$C_7$ uriedo; a $C_2$-$C_7$ carbamato; a $C_2$-$C_7$ carbonyl; a $C_1$-$C_7$ alkyl; a heteroatom containing $C_1$-$C_7$ alkyl; a $C_1$-$C_7$ alkyl having a substituent of N, O, or S; a $C_2$-$C_7$ alkenyl; a heteroatom containing $C_2$-$C_7$ alkenyl; a $C_2$-$C_7$ alkenyl having a substituent of N, O, or S; and B3 is: a $C_1$-$C_{20}$ alkyl, a heteroatom containing $C_1$-$C_{20}$ alkyl; $C_1$-$C_{20}$ alkyl having a substituent of N, O, or S; $C_4$-$C_{20}$ ether, $C_1$-$C_{20}$ ester; $C_1$-$C_{20}$ alkenyl; a heteroatom containing $C_1$-$C_{20}$ alkenyl; $C_2$-$C_{20}$ alkenyl having a substituent of N, O, or S; $C_1$-$C_{20}$ alkynl; a heteroatom containing $C_1$-$C_{20}$ alkynl; $C_2$-$C_{20}$ alkynl having a substituent of N, O, or S $C_6$-$C_{20}$ aryl; and $C_6$-$C_{20}$ heterocyclic containing a heteroatom of N, O or S. A substituent of N, O, or S is independently optionally a hydroxyl, an amino, a thiol, ether, thioether, or secondary amine.

Specificity of the substrate for a particular lysosomal enzyme is provided in part by structural variations in the sugar moiety A such as A being a monosaccharide or a disaccharide, and in some embodiments by the particular sugar moiety employed. Exemplary sugar moieties include β-D-Glucose for detecting Gaucher disease, and β-D-Galactose for detecting Krabbe disease. The monosaccharide is optionally linked to the remainder of the molecule by either a α or β glycosidic bond. Additional exemplary sugar moieties include but are not limited to allose, altrose, glucose, mannose, gulose, idose, galactose, talose, fructose, psicose, sorbose, and tagatose, each in either the D or L configuration.

$B^1$ is a linker moiety which functions to allow conjugation of the sugar moiety A to the remaining structure of the substrate. $B^1$ also functions as a spacer between the sugar moiety A and the remaining structure of the substrate so as to provide flexible access for a target enzyme. The linker arm $B^1$ can be designed so as to control the polarity of the materials and hence their solubility characteristics. In some instances, the linker arm $B^1$ can have a hydrophenol structure. Thus, a substrate of the general formula I can be configured to be at least partially hydrophilic in a solvent such as pure methanol or pure ethanol. The fatty acid moiety in toto generally is tailored to be sufficiently hydrophilic to provide aqueous solubility to the substrate. As such, the substrates can be soluble in aqueous buffer systems; although it is to be understood that, as is known in the art, detergents or other such agents may be included in the reagent mixture to enhance the aqueous solubility of the substrate materials.

$B^2$ provides aqueous solubility to the substrates relative to long chain fatty acids of natural cerebrosides or prior substrates. It was unexpected that the short alkyl chain length of particular $B^2$ structures (length of $C_2$-$C_7$) would allow recognition by the desired enzyme with sufficient affinity and turnover rate to be operable. In addition, the lack of saturation in the alkenyl chain according to some embodiments was similarly not expected to impart function as a substrate. Both of these elements used alone or separately allow full solubility characteristics to the substrates that was not achieved by prior methods.

In some embodiments, $B^2$ may include one or more a nucleophilic groups for interactions with a solid support or detectable tag, such as a fluorescent tag. Such nucleophilic groups are optionally a nitrogen, oxygen, or sulfur nucleophilic group. Optionally, a nucleophilic group is an amine.

A characteristic of the compositions is that they do not need to carry a quaternary ammonium group to be used in particular detection procedures such as mass spectroscopy. The relative solubility imparted by the $B^2$ group is sufficient to improve detection of one or more enzyme using the substrates. In comparison to previously described substrates, a substrate is generally more hydrophilic without the requirement of a permanently charged moiety and requires less or no need for detergent. This results in simplified assay procedures because, like the use of chloroform, the use of detergents can require cumbersome clean up steps including the labor-intensive liquid-liquid and solid phase extractions.

The specificity of the substrates during the mass spectrometry analysis may also be conferred by variations in the carbon length and degree of saturation within an alkyl group of $B^2$. Exemplary chemical structures of $B^2$ include a four-carbon fatty-acyl group for detecting Gaucher disease, and a six-carbon fatty-acyl group specific for detecting Krabbe disease. It is appreciated that absolute specificity for the enzyme is not imparted by $B^2$, but more appropriately by the identity of A. Different chain lengths or degree of saturation of $B^2$ can be used to tailor the substrates to the enzyme of interest as well as serve as a differentiator for detection in multiplex assay format. For example, a multiplex assay that combines a substrate with a $B^2$ including a four-carbon fatty-acyl group, and a second substrate with a $B^2$ having a six-carbon fatty-acyl group will allow detection and identification of which products is produced and which are not. For example, if a result indicates a four-carbon fatty-acyl group in a reaction product, this indicates the presence of β-glucerebrosidase in the material when using some embodiments of the substrates. If a result indicates a six-carbon fatty-acyl group this indicates the presence of a galactocerebroside β-galactosidase when using some embodiments of the substrates. Therefore, by combining substrates with different A groups and different product compositions, rapid identification of specific enzyme present in the sample is readily achieved.

A substrate is structurally terminated by a $B^3$ group. $B^3$ can be structurally tailored to provide different chain lengths. Such different chain lengths are useful for distinguishing different substrates, as well as enzymatic products thereof, from each other in enzyme assays. For example, in mass spectrometry, a substrate containing a 12 carbon atom chain has a different mass-to-charge ratio than a substrate containing a 14 carbon atom chain and as such, substrates containing 12 carbon atom or 14 carbon atom chains can be distinguished. Similarly, in immunoassay formats, substrates having differing chain lengths can be distinguished using antibodies selective for particular chemical moieties. It is recognized that the same is true for any differences in chain length or other structure of $B^3$ in the substrates when combinations of substrates are used in multiplex or singleplex assay formats.

In some embodiments, a substrate has the structure of:

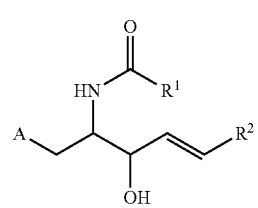

(II)

Where A is a monosaccharide or a disaccharide and is linked to the remainder of the molecule via a glycosidic bond; $R^1$ is a $C_1$-$C_6$ alkyl or a $C_2$-$C_{20}$ alkenyl, and where $R^2$ is a $C_{13}$-$C_{20}$ alkyl or a $C_{13}$-$C_{20}$ alkenyl. Optionally, $R^1$ is a $C_6$ alkyl or a $C_4$ alkyl, and $R^2$ is a $C_{13}$ alkyl. Optionally, A is an aldohexose or a ketohexose. Optionally, A is a D-glucose or D-galactose. Optionally, A is a D-glucose or D-galactose, $R^1$ is a $C_4$ alkyl, $C_5$ alkyl or a $C_6$ alkyl, and $R^2$ is a $C_{13}$-$C_{20}$ alkyl or a $C_{13}$-$C_{20}$ alkenyl. Optionally, A is a D-glucose or D-galactose, $R^1$ is a $C_4$ alkyl, $C_5$ alkyl or a $C_6$ alkyl, and $R^2$ is a $C_{13}$ alkyl.

In some embodiments, a substrate has the structure of:

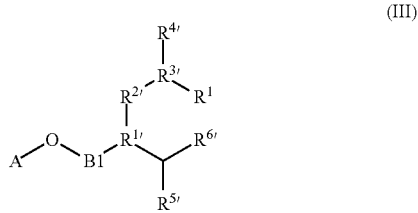

(III)

where A is a monosaccharide or a disaccharide; B1 is: a $C_1$-$C_{20}$ alkyl; a heteroatom containing $C_1$-$C_{20}$ alkyl, $C_2$-$C_{20}$ alkenyl; a heteroatom containing $C_2$-$C_{20}$ alkenyl; and a substituted or unsubstituted $C_6$-$C_{20}$ aryl; $R^{1'}$ is a substituted or unsubstituted C, or N; $R^{2'}$ is a substituted or unsubstituted C, a substituted or unsubstituted N, O, or S; $R^{3'}$ is a substituted or unsubstituted C, N, or O; $R^{4'}$ is a nullity, a substituted or unsubstituted $C_1$-$C_2$, O, or S; $R^1$ is: a $C_1$-$C_6$ alkyl; a heteroatom containing $C_1$-$C_7$ alkyl: a $C_1$-$C_7$ alkyl having a substituent of N, O, or S; a $C_2$-$C_7$ alkenyl; a heteroatom containing $C_2$-$C_7$ alkenyl; a $C_2$-$C_7$ alkenyl having a substituent of N, O, or S; $R^{5'}$ is a nullity, a substituted or unsubstituted $C_1$-$C_2$; O, or S; and $R^{6'}$ is a $C_1$-$C_{20}$ alkyl, a heteroatom containing $C_1$-$C_{20}$ alkyl; $C_1$-$C_{20}$ alkyl having a substituent of N, O, or S; $C_4$-$C_{20}$ ether, $C_1$-$C_{20}$ ester; $C_1$-$C_{20}$ alkenyl; a heteroatom containing $C_1$-$C_{20}$ alkenyl; $C_2$-$C_{20}$ alkenyl having a substituent of N, O, or S; $C_6$-$C_{20}$ aryl; and $C_6$-$C_{20}$ heterocyclic containing a heteroatom of N, O or S.

Figure 5:
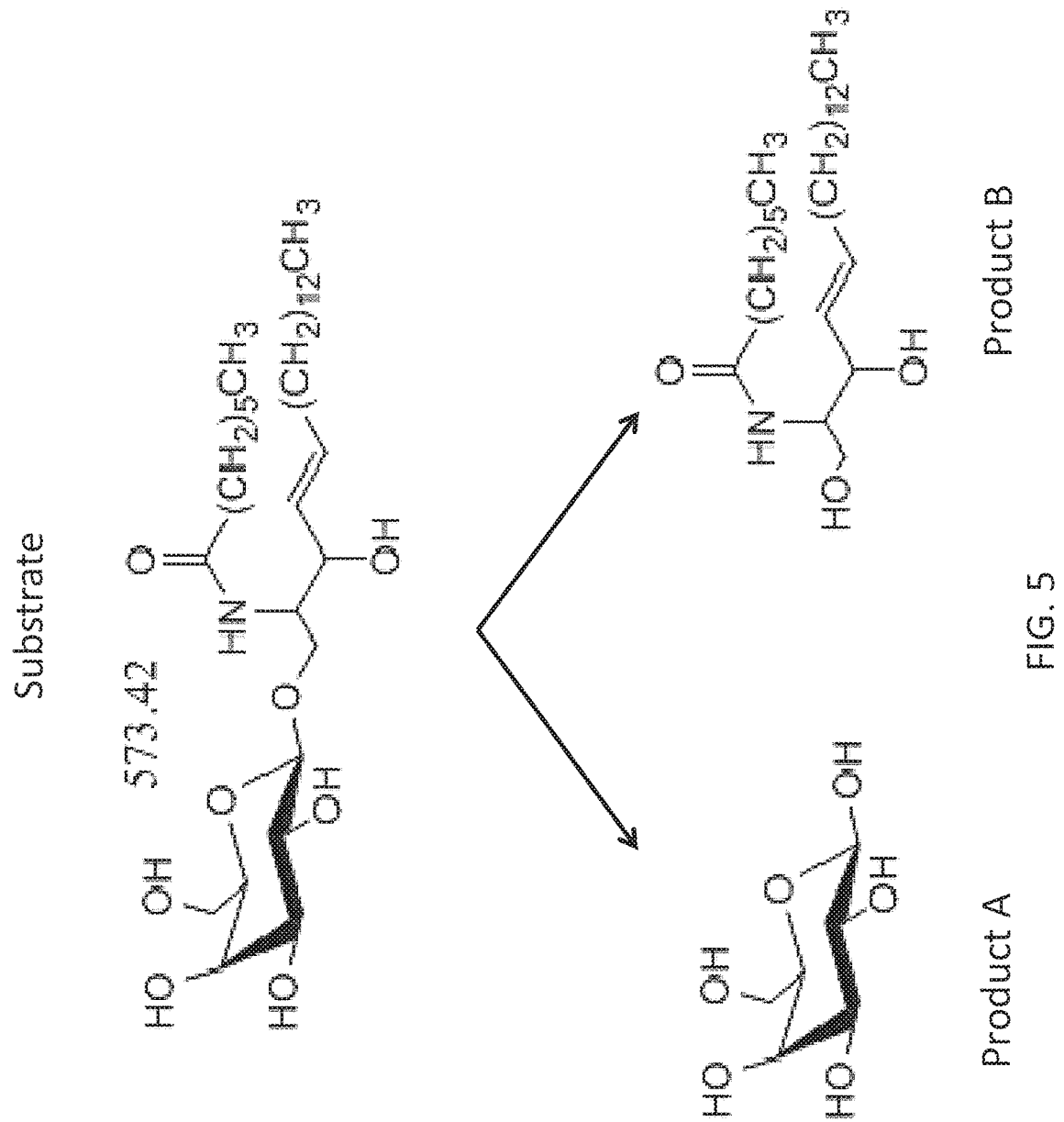
FIG. 5 is a generic enzymatic reaction scheme using an exemplary substrate.

Also provided are processes for detecting enzyme activity. The activity of a particular enzyme can be assessed by its capability or rate of acting on a cognate substrate to product enzymatic products. In the case of a substrate of Formula I-III, action of a target enzyme results in generation of two products: A (and/or A-H, since, as is shown in FIG. 5, the sugar group typically leave with an —OH group on the first carbon) and HO-fatty acid portion (B) since the B portion, as is shown in FIG. 5, also typically leaves in a hydroxylated form. By determining the amount of an enzymatic product in a sample, the activity of the target enzyme can be determined. For applications in which a quantitative assessment of enzymatic product is desired, a known amount of an internal standard corresponding to the non-A portion of Formula I-III, as is described in more detail below and is optionally labeled, can be included in the sample.

The activities of certain lysosomal enzymes in the blood of an individual can be used to test whether that individual has a lysosomal storage disorder. Therefore, substrates are provided for detecting medical conditions, in particular, lysosomal storage disorders such as Gaucher disease and Krabbe disease. For detecting Gaucher disease, an exemplary sugar moiety is β-D-glucose and an exemplary fatty acid portion (e.g. $B^1$(-$B^2$)-$B^3$)) includes a $B^1$ of methylene linked to a C7-amido and a substituent containing alkenyl of 1-20 carbons in length. For detecting Krabbe disease, an exemplary sugar moiety is β-D-galactose and an exemplary fatty acid portion includes a $B^1$ of methylene linked to a $C_5$-amido and a substituent containing alkenyl of 1-20 carbons in length.

A substrate can be tailored for assaying a variety of enzymes, in particular, enzymes associated with a disease state or birth defect, or one otherwise useful for medical purposes. Such tailoring is possible because a variety of monosaccharide and disaccharide groups can be present at A of the general formula I. Even for a newly identified target enzyme, once its specificity for monosaccharide and/or disaccharide groups is determined using routine methods, a substrate can be readily prepared using guidance provided herein. Non-limiting examples of enzymes which can be assayed using a substrate as described herein include acid β-glucocerebrosidase, galactocerebroside α-galactosidase, and acid sphingomyelinase.

As it is envisioned, one can synthesize substrates with different sugars, each specific to a particular lysosomal enzyme, and each having a different chain length in sub-group $B^2$ or $B^3$. This system provides for optional multiplex assays where two or more lysosomal enzymes are analyzed in the same sample or sample receptacle using structurally similar yet enzyme specific substrates.

The present invention provides compounds that function as experimental controls or standards useful for assessing the amount of enzymatic product in a sample or sample receptacle. For use in mass spectrometry methods, an internal standard corresponding to a particular substrate is structurally identical to its enzymatic product (i.e. fatty acid portion), except that the internal standard differs in mass-to-charge (m/z) ratio. Thus, the internal standards as provided include modified forms of enzymatic products, for example, stable isotope-labeled analogs of enzymatic products in which one or more atoms are replaced by corresponding atomic isotopes so as to create a differentially detectable mass difference with the corresponding enzymatic product. When the internal standard and enzymatic product are analyzed by mass spectrometry, the resulting spectrum reveals a spatial separation of the internal standard and enzymatic product, each represented by its own peak. The known amount of internal standard is reflected by peak magnitude at its known m/z ratio. The amount of enzymatic product can be assessed by comparison of peak magnitude at its known m/z, relative to the peak magnitude of the internal standard. An example of isotopic labeling to produce an internal standard is the replacement of $^1$H on an acyl group of B2 or B3 (or both) with $^2$H (i.e. deuterium, D). As a result, a "heavier" internal standard molecule with the substituted $^2$H has a different m/z from the enzymatic product, as detected on a mass spectrum. In a particular embodiment, an internal standard is labeled with deuterium to cause a mass change of 3 to 9 Daltons from the corresponding cleaved product In some embodiments the substrates are labeled with a detectable tag or a heavy atom label. A detectable tag may be found interacting with a $B^2$ group, a $B^3$ group, or both. Many fluorescent probes are recognized in the art as useful for labeling reactive amines. As such, some embodiments include a B2 group or a B3 group that terminates in a nucleophilic group suitable for interacting with a label or a substrate surface if desired. An illustrative nucleophilic group includes a nitrogen or oxygen nucleophile. A particularly sensitive target for specific labeling of biomolecules is a terminal amine group. A particular embodiment of the substrates includes a B2 or B3 that possesses this active terminal amino group. Illustrative examples of detectable tags suitable for labeling the substrates include fluorophores such as isothiocyanates, dansyl and other sulfonyl chlorides, 7-nitrobenz-2-oxa-1,3-diazole derivatives, fluorescamine, and the like.

A substrate can be used in a variety of physical formats, for example, in solution as well as linked or immobilized to solid supports. A solid support can be composed of a natural or synthetic material, an organic or inorganic material, such as a polymer, resin, metal or glass, and combinations thereof. A suitable solid support can have a variety of physical formats, which can include for example, a membrane; column; a hollow, solid, semi-solid, pore or cavity-containing particle such as a bead; a gel; a fiber, including a fiber optic material; a matrix and sample receptacle. Non-limiting examples of sample receptacles include sample wells, tubes, capillaries, vials and any other vessel, groove or indentation capable of holding a sample. A sample receptacle can be contained on a multi-sample platform, such as a microplate, slide, microfluidics device, and the like. Many suitable particles are known in the art and illustratively include Luminex®-type encoded particles, encoded fiber optic particles, magnetic particles, and glass particles. Covalent interaction of a substrate and/or enzymatic cleavage product thereof with a solid support is useful for retaining the substrate and/or product during washing procedures performed in some assay formats, thus, producing a robust and accurate signal of enzymatic activity.

When use of a solid support is desired for an assay format, the presence of the exemplary amine terminated $B^2$ or $B^3$ group can be used, for example, for covalent bonding to high-binding solid supports. High binding solid supports are surfaces having exposed moieties that are chemically active or otherwise capable of covalent or high affinity binding to a substrate or internal standard. As an example, Corning Life Sciences produces high-binding microwell plates that are irradiated to break the benzene ring and produce exposed carboxylic acids. These carboxylic acids are amenable to nucleophilic attack such as by the terminal amino group on the lysine derivative component of an embodiment substrate. This reaction is rapid and produces a tight interaction between the substrate/product and the high-binding surface.

The methods described herein and compositions provided can be performed in a multiplexed format such that a plurality of samples are assayed simultaneously. An illustrative multiplexed format involves using physically and/or chemically coded particles. Use of coded particles in multiplexed formats has been described, for example, in U.S. Pat. Nos. 6,649,414 and 6,939,720. Because the codes allow particles to be distinguished from each other, a plurality of distinct particles can be present in a single reaction mixture, allowing a plurality of different samples or different enzymes to be assayed simultaneously. Codes on particles can correspond, for example, to sample origins, particular enzymes to be assayed, particular substrates present, and the like, depending on the experimental goal of the user.

A sample useful in the processes provided contains or is suspected of containing one or more target enzymes. Target enzymes can be contained in samples obtained from an individual, as well as from laboratory materials, such as cell lines, and synthetic protein sources. Exemplary sample sources illustratively include: tissue homogenates; cell culture lysates; and biological fluids including urine, blood in liquid or dry form, tears, saliva, and cerebrospinal fluid. A sample can be further fractionated, if desired, to a fraction containing particular cell types. For example, a blood sample can be fractionated into serum or into fractions containing particular types of blood cells such as red blood cells or white blood cells (leukocytes). If desired, a sample can be a combination of samples from a subject such as a combination of a tissue and fluid sample, and the like. In a specific embodiment, the sample is blood, which can be, for example, whole blood or a blood fraction thereof, or reconstituted from a dry blood sample.

Methods for obtaining samples that preserve the activity or integrity of molecules in the sample are well known to those skilled in the art. Such methods include the use of appropriate buffers and/or inhibitors, including nuclease, protease and phosphatase inhibitors, which preserve or minimize changes in the molecules in the sample. Such inhibitors include, for example, chelators such as ethylenediamine tetraacetic acid (EDTA), ethylene glycol bis(P-aminoethyl ether)N,N,N1,N1-tetraacetic acid (EGTA), protease inhibitors such as phenylmethylsulfonyl fluoride (PMSF), aprotinin, leupeptin, antipain and the like, and phosphatase inhibitors such as phosphate, sodium fluoride, vanadate and the like. Appropriate buffers and conditions for isolating molecules are well known to those skilled in the art and can be varied depending, for example, on the type of molecule in the sample to be characterized (see, for example, Ausubel et al. Current Protocols in Molecular Biology (Supplement 47), John Wiley & Sons, New York (1999); Harlow and Lane, Antibodies: A Laboratory Manual (Cold Spring Harbor Laboratory Press (1988); Harlow and Lane, Using Antibodies: A Laboratory Manual, Cold Spring Harbor Press (1999); Tietz Textbook of Clinical Chemistry, 3rd ed. Burtis and Ashwood, eds. W.B. Saunders, Philadelphia, (1999)). A sample also can be processed to eliminate or minimize the presence of interfering substances.

Samples in the form of a dry blood spot are commonly used when screening blood from newborns and child patients. To prepare these samples, blood is collected and retained on filter paper. For analysis, the dried blood is eluted from the filter paper into an aqueous solution, which generally contains a buffer such as phosphate buffered saline and a protease inhibitor. Specific examples of protease inhibitor conditions include for example, one or more of the following: AEBSF hydrochloride in a final concentration of 50 to 400 µg/ml, EDTA disodium dehydrate in a final concentration of 0.2 to 25 mg/ml, leupeptin hemisulfate in a final concentration of 0.5 to 1 µg/ml, and pepstatin A in a final concentration of 0.5 to 1 µg/ml. Protease inhibitor cocktails known commonly used in the art may be used. The use of a universal assay solution to extract a single dry blood sample, or other type of sample, for subsequent distribution into multiple assay reactions can be used for automatic and high throughput screening. A single extraction of a dry sample avoids the need to obtain several sample punches from the same sample, or to collect aliquots of other sample sources and accordingly reduces variation caused by inhomogeneous distribution of blood on the filter paper and errors in sample transfer. When using dry samples, extraction efficiency may vary with the different enzymes being analyzed. In these and other types of samples, the target enzymes may have different levels of activities when contained in different assay solutions. A composition of a universal assay solution is optionally chosen such that each enzyme to be tested is active.

In some embodiments, the dried blood spot or a punch derived from it is placed directly into an assay buffer including one or more substrates and optionally internal standards or and allowed to incubate for a time sufficient to allow enzymes present in the sample to convert the substrate(s) to product(s) prior to detection by one or more detection methods.

The substrates and products provided can be used in a variety of assay formats. The substrate can be detected in an assay when it is desired to observe substrate consumption during an enzymatic assay, while the product can be detected in the assay when it is desired to observe its formation during an enzymatic assay. Both substrate and product can be detected when it is desired to observe the enzymatic reaction from both perspectives, for example, to confirm that the amount of product produced correlates with the amount of substrate consumed.

For example, the amount of substrate or product can be detected using established tandem mass spectrometry procedures. An exemplary enzyme assay employing mass spectrometry can be performed as follows. A sample is incubated with a substrate for a time period that allows formation of an enzymatic product. During the incubation period, the substrate is cleaved by a target enzyme present in a blood sample to form a respective product. The reaction is then quenched by adding a reagent that precipitates protein components. Exemplary reagents include alcohol, acetonitrile and dilute trifluoro acetic acid. A portion of the incubation mixture is then transferred to a new assay vessel. Optionally, a dilution reagent such as methanol, acetonitrile, water-methanol mixtures or water-acetonitrile can be added to dilute the transferred portion. The sample so diluted reduces the amount of endogenous competing material so as to relatively increase the sensitivity of the tandem mass spectrometry analysis. Other types of reagents are selected by those skilled in the art to be compatible with analyses by mass spectrometry of many varieties.

In some embodiments, the diluted sample is directly injected into the tandem mass spectrometer either manually or automatically with the aid of autosamplers and liquid handlers. If desired, the sample can be derivatized prior to analysis. Reagents are selected to be non-hostile to the MS/MS system. For example, suitable solvents lack detergents and corrosive agents, such as chloroform. Pure ethanol and pure methanol are often used simply because they easily vaporized upon mechanical drying processes.

The tandem mass spectrometer can be set to simultaneously detect the added substrate, the corresponding resulting enzymatic product and the corresponding internal standards. Such detection is accomplished by means of parent ion scans, precursor ion scans or multiple reaction monitoring scans.

The amount of substrate consumed or product formed during an enzymatic assay also can be detected using antibodies and other target-specific binding molecules. For immunoassays, an antibody can be used to detect the substrate, product or both. Antibodies useful in such methods can be specific, such that they recognize individual substrates, or non-specific, such that they recognize many or all substrates. A substrate or product optionally includes a label such as biotin or avidin to allow specific detection.

The antibody is illustratively produced in animals including mouse, rat, rabbit, horse, donkey, or other suitable animal used for the production of antibodies. In some applications, it is useful to label an antibody with a detectable tag, such as a fluorescent tag. When using an unlabeled antibody, detection can be performed by using a secondary antibody that is specific for the species IgG of the primary antibody is labeled illustratively with a fluorescent marker such as rhodamine. It is appreciated in the art that other antibody detection systems are similarly operable in the instant invention such as horseradish peroxidase labeled antibodies, or alkaline phosphatase labeled antibodies.

When testing multiple enzymes in a single sample by providing multiple enzyme-specific substrates, antibodies that recognize and distinguish between the substrates, or products thereof, and be used. Complexes of antibodies bound to enzyme-specific substrates, or products thereof, can be distinguished from each other using many methods. In one scenario, samples containing target enzymes are contacted with substrates linked to particles in an assay solution. In this example, each particle is linked to a particular substrate, and there are multiple particles representing each substrate. The target enzymes act on the substrates to produce products (A) and the fatty acid containing portion of the molecule (B). The product remains bound to the particle, while the A product is released into solution. Antibodies that recognize specific products are then contacted with the assay solution. The antibodies will bind to the products, if produced during the enzymatic assay, to produce particles having bound antibodies. To distinguish different products contained on the particles, antibodies having different product specificities can have different detectable moieties, such as different fluorescent tags. As an alternative to detecting enzymatic products, antibodies that recognize substrate can be used to detect substrate remaining on the beads after incubation with enzymes. In this situation, either product would remain attached to the bead, if an enzymatic reaction occurred. In either case the selected substrate specific antibody would not significantly cross-react with product attached to the bead.

In another scenario, samples containing target enzymes are contacted with substrates linked to encoded particles in an assay solution. The encoded particles have a feature, such as a bar code or optical profile, which allows them to be distinguished from each other. For example, encoded particles can have different bar codes corresponding to different target enzyme substrates. In the assay, the target enzymes act on the substrates to produce products. The fatty acid product would remain bound to the particle, while the A product would be released into solution, or visa versa. Antibodies that recognize specific products are then contacted with the assay solution. Because the encoding of the particle indicates which substrate is attached to the particle, antibodies need not be specific for particular products, and thus one type of antibody can be used to detect products derived from multiple different substrates. Such non-specific antibodies will bind to the products, if produced during the enzymatic assay, to produce particles having bound antibodies. Particles having bound antibodies are then distinguished from those without antibodies, for example, by detecting a tag on the antibodies or physical behavior of the particles. The different products contained on the antibody-bound particles can be determined based on the encoding of each particle.

As another example of an immunoassay format, antibodies directed to particular substrates are generated. Following quenching of an enzymatic reaction, the reaction solution is transferred to a high-binding microtiter plate whereby the reactive $B^2$ moiety (for example) covalently attaches to the plate via a terminal amino group. The enzyme and assay solution components are removed by washing. The specific primarily antibody is then incubated in each assay well followed by subsequent washing to remove unbound antibody. A secondary antibody is optionally used for detection and quantitation. The more product formed per unit time of initial reaction the greater the activity of the measured enzyme.

In an alternative immunoassay format, an antibody specific for the fatty acid subgroup is optionally used as a capture antibody on the surface of the microtiter plate in a standard sandwich ELISA assay. A primary antibody with a unique epitope on the product such as one directed to the fatty acid moiety (or the fatty acid moiety is modified with a specific binding pair member such as biotin) is used for detection. As is recognized in the art, a labeled secondary antibody is optionally used for detection as described above.

In an additional immunoassay format, an exemplary antibody reacts with the α-D-glucose A group bound to the $B^1$ moiety. The substrate may be attached to a solid support using an amino terminated fatty acid moiety. Alternatively, the substrate is provided in solution, the reaction is transferred to a sample receptacle, in which following quenching of an exemplary enzymatic reaction, the reaction solution is transferred to a high-binding microtiter plate whereby the reactive fatty acid moiety covalently attaches to the receptacle via a terminal amino group. As another alternative, a capture antibody specific for an alternate epitope on the product/substrate is employed. The unreacted enzyme and buffer components are removed by washing. The antibody specific to the A-$B^1$ moiety is then incubated in each assay well for detection and quantitation of remaining substrate. The greater the substrate remaining after the initial enzyme reaction, the lower the activity of the enzyme.

The antibody is illustratively unlabeled and produced in animals including mouse, rat, rabbit, horse, donkey, or other suitable animal used for the production of antibodies. A secondary antibody that is specific for the species IgG of the primary antibody is labeled illustratively with a fluorescent marker such as rhodamine and subsequently used for detection of remaining substrate. It is appreciated in the art that other antibody detection systems are similarly operable in the instant invention such as horseradish peroxidase labeled antibodies, or alkaline phosphatase labeled antibodies.

In another example of a suitable immunoassay format, monoclonal mouse antibody specific for the exemplary the α-D-glucose A group bound to the $B^1$ moiety and/or to a portion of a fatty acid moiety is itself labeled illustratively by a fluorescent marker. In this system multiple lysosomal enzymes are optionally simultaneously analyzed for activity toward a variety of specific substrates. An illustrative example includes a two enzyme system wherein two substrate are employed, one specific for GALC and another specific for ABG. Each substrate is simultaneously added to the reaction with the biological sample. As each substrate optionally contains an amine terminated fatty acid group, both will similarly bind to the high-binding microtiter plate. Two antibodies, each specific for its respective substrate are added to the microtiter plate following washing as above. Each antibody is illustratively labeled with a different fluorophore such as rhodamine or cyanine. As such the binding of each antibody is detected and quantitated without interference from the other, and the amount of each enzyme activity is detectable in the same well of the microtiter plate from the same sample.

In some embodiments, an assay for target enzymes is performed by first obtaining a sample illustratively including serum, plasma, whole blood, urea, saliva, other biological fluids or tissue lysates, recombinant or native purified enzyme in solution, or chemically or functionally modified enzyme in biological fluid or liquid medium. A portion of the filter paper sample is then excised and deposited in a non-binding assay tube or micro titer plate well to which an assay solution is added. The assay solution comprises aqueous buffers, a substrate, a standard, as well as protease inhibitors. The sample mixture is then incubated for a determined period of time in the range of 30 minutes to 20 hours at a particular temperature ranging from 30 to 41° C. Once incubation is complete, the enzymatic reaction is terminated by addition of a stopping solution. A stopping solution is illustratively 0.4 M glycine/NaOH pH 10.4 added at 6× reaction volume. Leonard R, et al., *J. Biol. Chem.*, 2006; 281:4867-75; Boot, R G, et al., *J. Biol. Chem.*, 2006; 282:1305-12. The amount of product formation is determined by transferring a known volume of sample to a high-binding assay tube or microtiter plate and incubated for 5 minutes to 2 hours. The unbound material is removed by washing. Detection of the intact substrates or products is illustratively performed using a coupled peroxidase enzyme approach.

In a further scenario, the level of released glucose or galactose product is measured in real time by a coupled enzyme approach. A non-limiting example involves the release of glucose from a substrate specific for β-glucocereborsidase in diagnosis of Gaucher disease. In this assay method glucose is reacted with glucose oxidase producing glucolactone and releasing hydrogen peroxide. The released hydrogen peroxide is detected by reaction with peroxidase to produce a fluorescent molecule that is measured on a standard fluorometer. Examples of suitable peroxidases are horseradish peroxidase or any other peroxidase known in the art. The hydrogen peroxide released by glucose oxidase interacts with a detector substrate molecule. The peroxidase catalyzes conversion of this substrate to a fluorescent product. A detector molecule suitable for use with the substrates includes Amplex Red that is oxidized in to produce the fluorescent product resorufin. Amplex Red and kits for detecting free glucose are available from Invitrogen Corp. The increase in red fluorescent product is detected on a fluorometer set with an excitation wavelength at 571 and an emission wavelength at 585 with the band pass set at 5 nm. The greater amount of glycosidase activity the more rapidly the red fluorescent product is produced.

In some embodiments multiple substrates for different lysosomal enzymes are generated with unique fatty acid structure(s). This prevents product inhibition of one enzyme that is particularly important should the catalytic activity of one enzyme toward one substrate be much greater than the catalytic activity of the other enzyme for its corresponding substrate. This is additionally important in conditions where a single mutant glycosidase is being screened in a panel of substrates for 6 or more lysosomal enzymes. The product formed by the other lysosomal enzymes may inhibit the function of the lower activity enzyme such that its activity is not accurately measured. Thus, the specificity of the substrate and the product for each enzyme is appreciated to be optionally distinct.

When more than one enzyme is detected simultaneously by combining multiple substrates directed to respective enzymes, the substrates may differ not only in the type of sugar moiety which confers enzyme specificity, but also in the length of the any component of the fatty acid portion. This is particularly important with the use of MS/MS as a detection tool since the differentiated substrate molecules having corresponding differentiated mass index correspond to various enzymes being examined.

The approach described for assaying enzymes using the described substrate and standard compounds can be expanded to assay a plurality of enzymes simultaneously in a single reaction, obviating the need for multiple assays to assist in confirming diagnoses of medical disorders. The methods can also be used to measure several enzymes simultaneously when evaluating the rate of chemical flux through a specific biochemical pathway or for monitoring biochemical signaling pathways. Because of the high sensitivity of mass spectrometry detection employable using the compounds described herein, which can require only sub-microgram quantities of the substrate reagents per assay, the synthesis of several hundred substrate reagents on a low-gram scale becomes practical and economical.

In various embodiments two, three, four, five, six, or more lysosomal enzymes are simultaneously measured for activity by the use of substrates as provided.

As another exemplary format for use with the provided substrates, the substrates can be labeled with the same fluorophore, but possess significant mass or charge characteristics that differentiate one from the other. The amount of product produced following an enzymatic cleavage reaction is detected by reversed phase high performance liquid chromatography (HPLC). Reactions are quenched by the addition of alcohol, acetonitrile or dilute trifluoro acetic acid. A portion of the incubation mixture is transferred to a new assay vessel to which is added a neat solution such as methanol, acetonitrile, water-methanol mixtures or water-acetonitrile. The reaction products and unreacted substrate are separated on a 5 μm particle size $C_{18}$ HPLC column and detected by a fluorescent detector or set of detectors. The amount of product is calculated based on a standard curve generated using increasing amounts of the relevant product.

It is appreciated in the art that multiple substrates for multiple enzymes are optionally simultaneously detected by a chromatographic method. If substrates with sufficiently different mass or retention characteristics are used, each product is resolvable, for example, on an HPLC column and can be quantified in a single assay. Alternatively, each substrate is labeled with a different fluorophore that has different or the same excitation or emission properties. Detection may be by a family of fluorescent detectors that can simultaneously quantify individual products from each other and their corresponding labeled substrate. Other methods of detection are similarly suitable and are known in the art.

Figure 2:
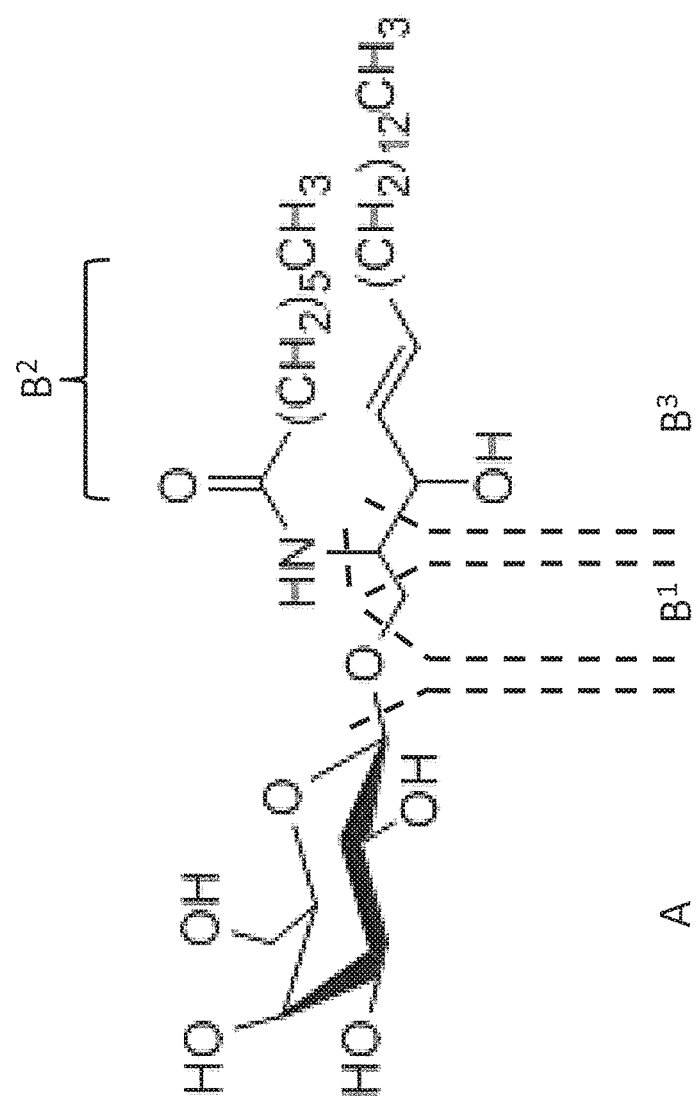
FIG. 2 is an exemplary substrate structure highlighting structural moieties.

FIG. 2 depicts an exemplary substrate structure for detecting lysosomal storage disorders. The structure is composed of a sugar (A) in the form of a glucose or a galactose where galactose is illustrated and an aliphatic group B. Group B includes a linker arm ($B^1$) in the form of a methylene, a $B^2$ subgroup of a $C_5$-amido, and a $B^3$ subgroup in the form of an alkenyl with carbon length in the range of 10 to 30 and a substituent of O. It is appreciated that the structure of FIG. 2 can also be described in relation to Formula III as one exemplary embodiment thereof.

Figure 3:
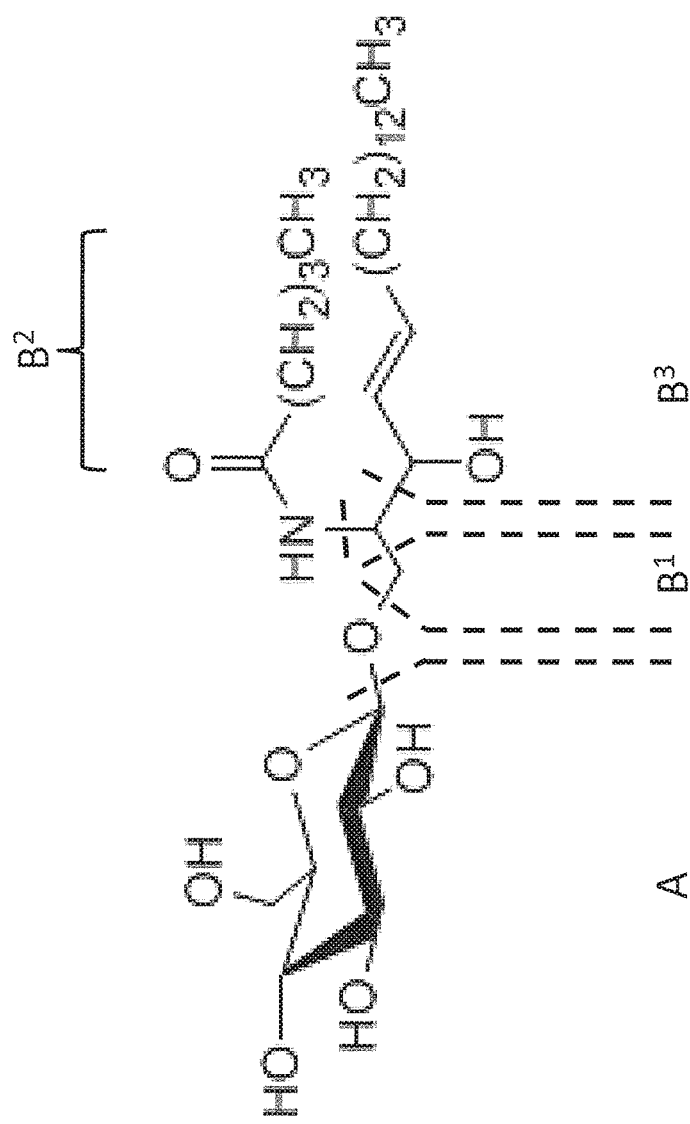
FIG. 3 is an exemplary substrate structure highlighting structural moieties.
Figure 4:
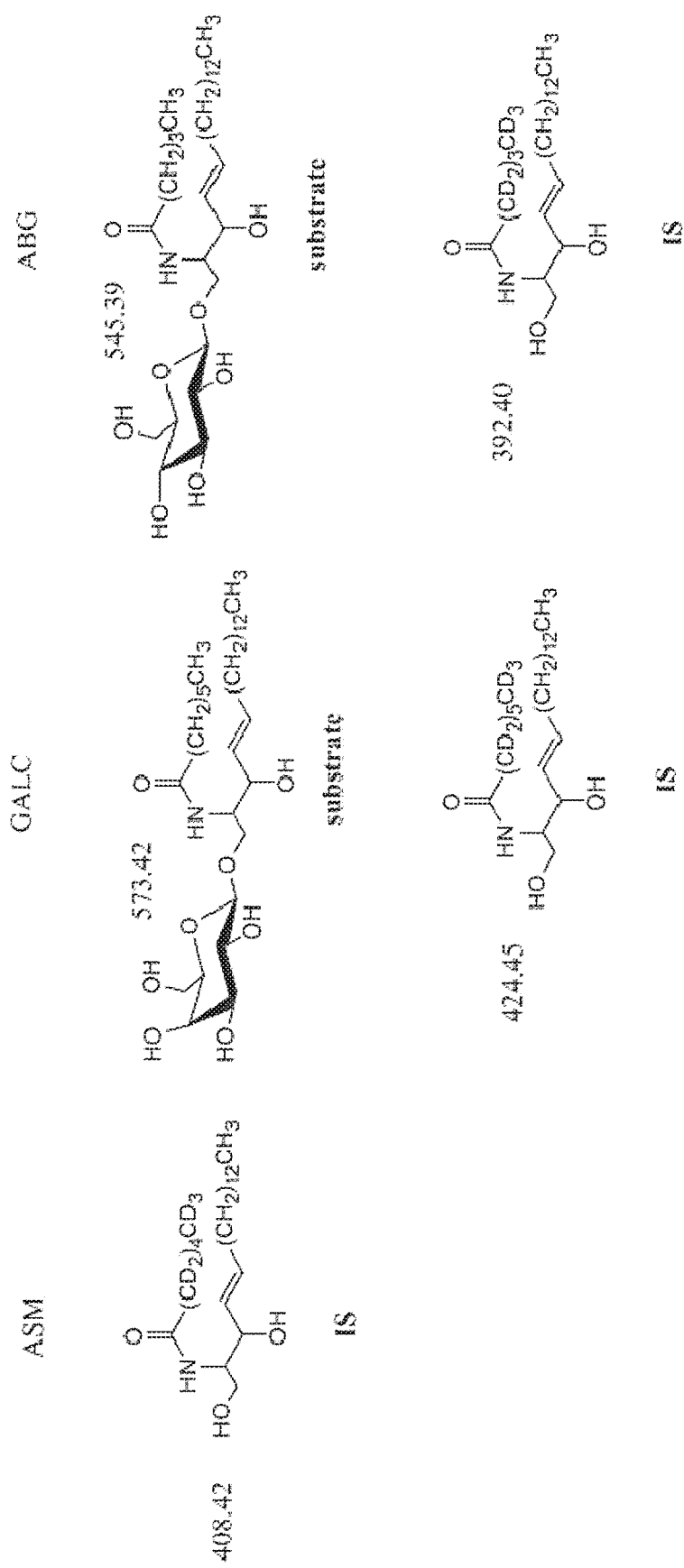
FIG. 4 illustrates exemplary substrate structures and corresponding exemplary internal standard structures.

FIG. 3 depicts an exemplary substrate structure for detecting lysosomal storage disorders. The structure is composed of a sugar (A) in the form of a glucose or a galactose where galactose is illustrated and an aliphatic group B. Group B includes a linker arm ($B^1$) in the form of a methylene, a $B^2$ subgroup of a $C_7$ amido, and a $B^3$ subgroup in the form of an alkenyl with carbon length in the range of 10 to 30 and a substituent of O. It is appreciated that the structure of FIG. 3 can also be described in relation to Formula III as one exemplary embodiment thereof.

FIG. 5 demonstrates a generic enzymatic reaction using an exemplary substrate. Upon specific affinity binding and enzymatic reaction, the substrate is cleaved into two groups, a sugar moiety A and an aliphatic group B. The group B is optionally composed of amide and long-chain alkyl or alkenyl moieties. Both groups are optionally then analyzed by MS/MS. An internal standard is also concurrently subject to the MS/MS analysis. The internal standard is optionally an isotopically labeled analog of B with deuterium to replace hydrogen atom(s) on a methyl group or other portion of the molecule.

Also provided is a compound having utility as an internal standard or control for detecting activity of an enzyme having the formula:

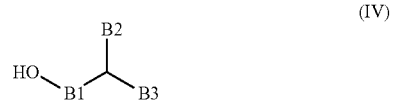

where B1 is: a $C_1$-$C_{20}$ alkyl; a heteroatom containing $C_1$-$C_{20}$ alkyl, $C_2$-$C_{20}$ alkenyl; a heteroatom containing $C_2$-$C_{20}$ alkenyl, a substituted or unsubstituted $C_6$-$C_{20}$ aryl; B2 is: a $C_2$-$C_7$ urethane; a $C_2$-$C_7$ amido, a $C_2$-$C_7$ ester, a $C_2$-$C_7$ uriedo; a $C_2$-$C_7$ carbamato; a $C_2$-$C_7$ carbonyl; a $C_1$-$C_7$ alkyl; a heteroatom containing $C_1$-$C_7$ alkyl; a $C_1$-$C_7$ alkyl having a substituent of N, O, or S; a $C_2$-$C_7$ alkenyl; a heteroatom containing $C_2$-$C_7$ alkenyl; a $C_2$-$C_7$ alkenyl having a substituent of N, O, or S; and B3 is: a $C_1$-$C_{20}$ alkyl, a heteroatom containing $C_1$-$C_{20}$ alkyl; $C_1$-$C_{20}$ alkyl having a substituent of N, O, or S; $C_4$-$C_{20}$ ether, $C_1$-$C_{20}$ ester; $C_1$-$C_{20}$ alkenyl; a heteroatom containing $C_1$-$C_{20}$ alkenyl; $C_2$-$C_{20}$ alkenyl having a substituent of N, O, or S; $C_1$-$C_{20}$ alkynl; a heteroatom containing $C_1$-$C_{20}$ alkynl; $C_2$-$C_{20}$ alkynl having a substituent of N, O, or S $C_6$-$C_{20}$ aryl; and $C_6$-$C_{20}$ heterocyclic containing a heteroatom of N, O or S. A substituent of N, O, or S is independently optionally a hydroxyl, an amino, a thiol, ether, thioether, or secondary amine.

In some embodiments, The structure $B^1$-$B^2$-$B^3$ has the structure of:

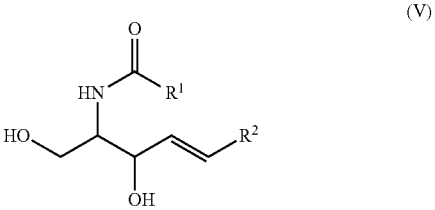

where $R^1$ is a $C_1$-$C_6$ alkyl or a $C_2$-$C_{20}$ alkenyl, and where $R^2$ is a $C_1$-$C_{20}$ alkyl; a $C_1$-$C_{20}$ alkenyl; a $C_1$-$C_{20}$ alkyl having a substituent of N, O, or S, a $C_1$-$C_{20}$ alkenyl, or a $C_1$-$C_{20}$ alkenyl having a substituent of N, O or S; and $R^2$ is as defined for Formula II. Optionally, $R^1$ is a $C_6$ alkyl or a $C_4$ alkyl, and $R^2$ is a $C_{13}$ alkyl. Optionally, $R^1$ is a $C_4$ alkyl, $C_5$ alkyl or a $C_6$ alkyl, and $R^2$ is a $C_{13}$-$C_{20}$ alkyl or a $C_{13}$-$C_{20}$ alkenyl. Optionally, $R^1$ is a $C_4$ alkyl or a $C_6$ alkyl, and $R^2$ is a $C_{13}$ alkyl. The compositions of Formula V optionally include one or more stable secondary prevalence isotopes that are optionally $^2H$, $^{13}C$, $^{15}N$, $^{17}O$, $^{18}O$, $^{31}P$, $^{34}S$, or combinations thereof.

Specific illustrated embodiments of an internal standard according to the invention include but are not limited to:

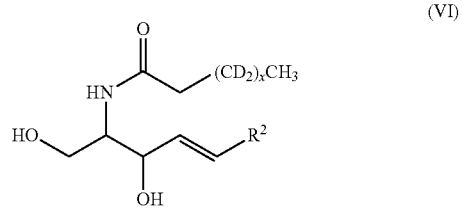

where x is a value between 2 and 4, and where $R^2$ is a $C_1$-$C_{20}$ alkyl, a $C_1$-$C_{20}$ alkenyl, or a $C_1$-$C_{20}$ alkynl, any of which may be substituted with an N, O, or S, or include a substituent of N, O, or S. Optionally, x is 2 or 4 and $R^2$ is a $C_{13}$ alkyl. It is further appreciated that in some embodiments, the heavy isotope is optionally present on the α-carbon in the amido group, on any position on the hydroxyl containing aliphatic group, or any combination thereof.

It is further appreciated that the compound of Formula V or VI is also functional as an antagonist, an analytical control, or for clinical treatment of disease such as hypothyroidism, diabetes, and HIV.

In an alternative embodiment the substrates of Formulas I-III are optionally synthesized with a non-hydrolyzable link between A and $B^1$. This produces suicide substrates that maintain high specificity for their target lysosomal enzyme. These molecules serve as more specific and potent inhibitors of enzyme function.

All reagents including the substrates, enzymatic products, and internal standards can be optionally purified by reverse-phase HPLC and characterized by ESI-MS, either in an online HPLC-MS assay or offline by collection of the appropriate fractions.

Various aspects of the present invention are illustrated by the following non-limiting examples. The examples are for illustrative purposes and are not a limitation on any practice of the present invention. It will be understood that variations and modifications can be made without departing from the spirit and scope of the invention. Reagents illustrated herein are commercially available or readily synthesized by well-known methods from readily commercially available precursors, and a person of ordinary skill in the art readily understands where such reagents may be obtained.

EXAMPLES

Example 1

Preparation of Substrates

Preparation of Compound 1 is achieved substantially as depicted in Scheme I:

Briefly, α-D-glucose modified sphingosine (A) (D-glucosyl-β1-1'-D-erythro-sphingosine, Avanti Polar Lipids, Alabaster, Ala.) is dissolved in 1 mL of dry DMF (Aldrich). 1.5 eq. of pentanoyl-NHS ester (B) was added (from a 50 mg/mL stock solution in DMF, stored −20° C.). The reaction is completed in 2 minutes as measured by TLC. The reaction product was subjected to centrifugation in a Speed-Vac overnight without heating. The residue was taken up in 1-1.4 mL DMF and injected in 6-7 portions onto a HPLC column (Vydac C18 column (218TP1022, 22×250 mm) run at 6 mL/min). The column was run using solvent A of 25% methanol in water and solvent B of 20% methanol in acetonitrile in a gradient of 35-100% B over 30 min, then held at 100% B for 30 min. Product is detected by UV at 213 nm. Product fractions were pooled from all HPLC runs, and solvent was removed in a centrifugal concentrator (Speed-Vac, oil pump vacuum, room temperature) to give the desired product of compound 1 in near quantitative yield

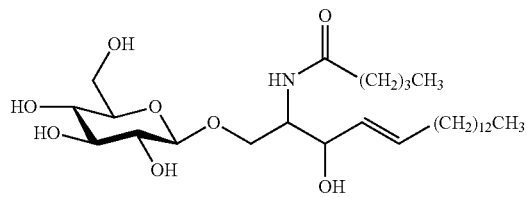

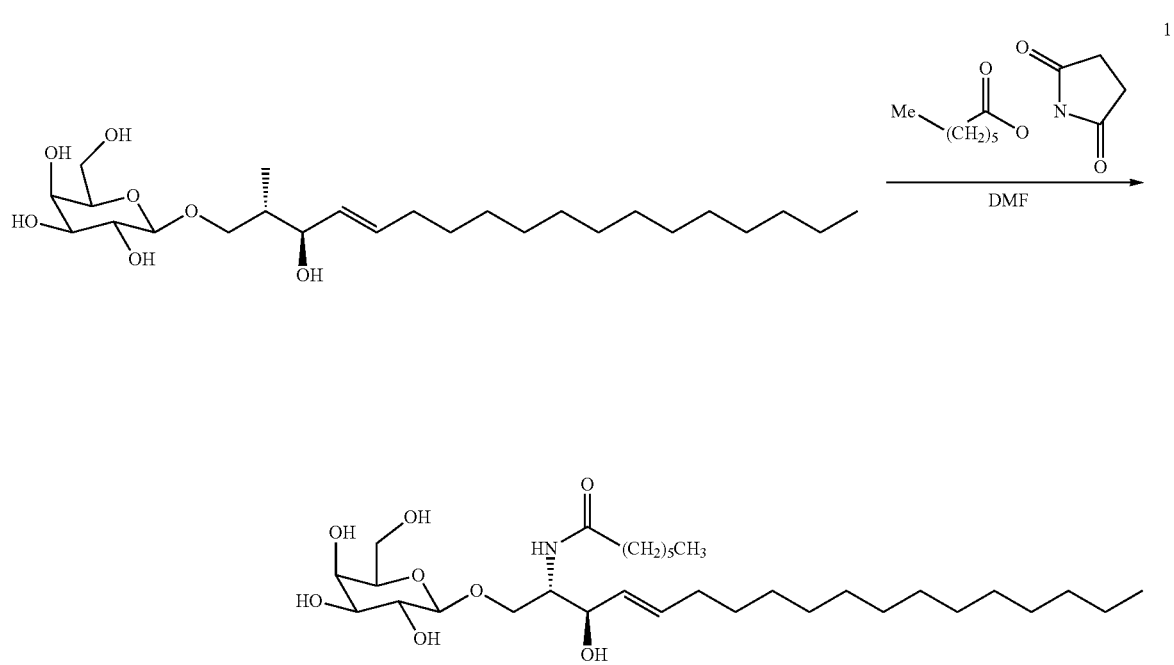

The resulting Compound 1 is analyzed by NMR to confirm identity. Results are demonstrated in FIG. 1A. The observed molecular weight of the resulting compound is 545.3948. The above process is similarly used to synthesize other compounds by substituting the pentanoyl-NHS ester with those of varying alkyl chain lengths.

Additional compounds according to Formula II synthesized are presented in Table 1:

TABLE 1

| Compound | A | $R^1$ alkyl chain length | $R^2$ alkyl chain length | NHS ester |
|---|---|---|---|---|
| 1 | Glucose | $C_4$ | $C_{13}$ | pentanoyl |
| 2 | Glucose | $C_3$ | $C_{13}$ | butyroyl |
| 3 | Glucose | $C_5$ | $C_{13}$ | hexanoyl |
| 4 | Glucose | $C_6$ | $C_{13}$ | heptanoyl |
| 5 | Glucose | $C_7$ | $C_{13}$ | octanoyl |
| 6 | Galactose | $C_3$ | $C_{13}$ | butyroyl |
| 7 | Galactose | $C_4$ | $C_{13}$ | pentanoyl |
| 8 | Galactose | $C_5$ | $C_{13}$ | hexanoyl |
| 9 | Galactose | $C_6$ | $C_{13}$ | heptanoyl |
| 10 | Galactose | $C_7$ | $C_{13}$ | octanoyl |

The above processes are repeated by varying the $R^2$ alkyl chain lengths from 14 to 20 carbons to synthesize compounds 11-80 listed in groups of 10 with each $R^2$ alkyl chain length as in Table 1 respectively. Confirmation of the identity and structures of the thus prepared compounds were obtained through NMR analysis.

Figure 1B:
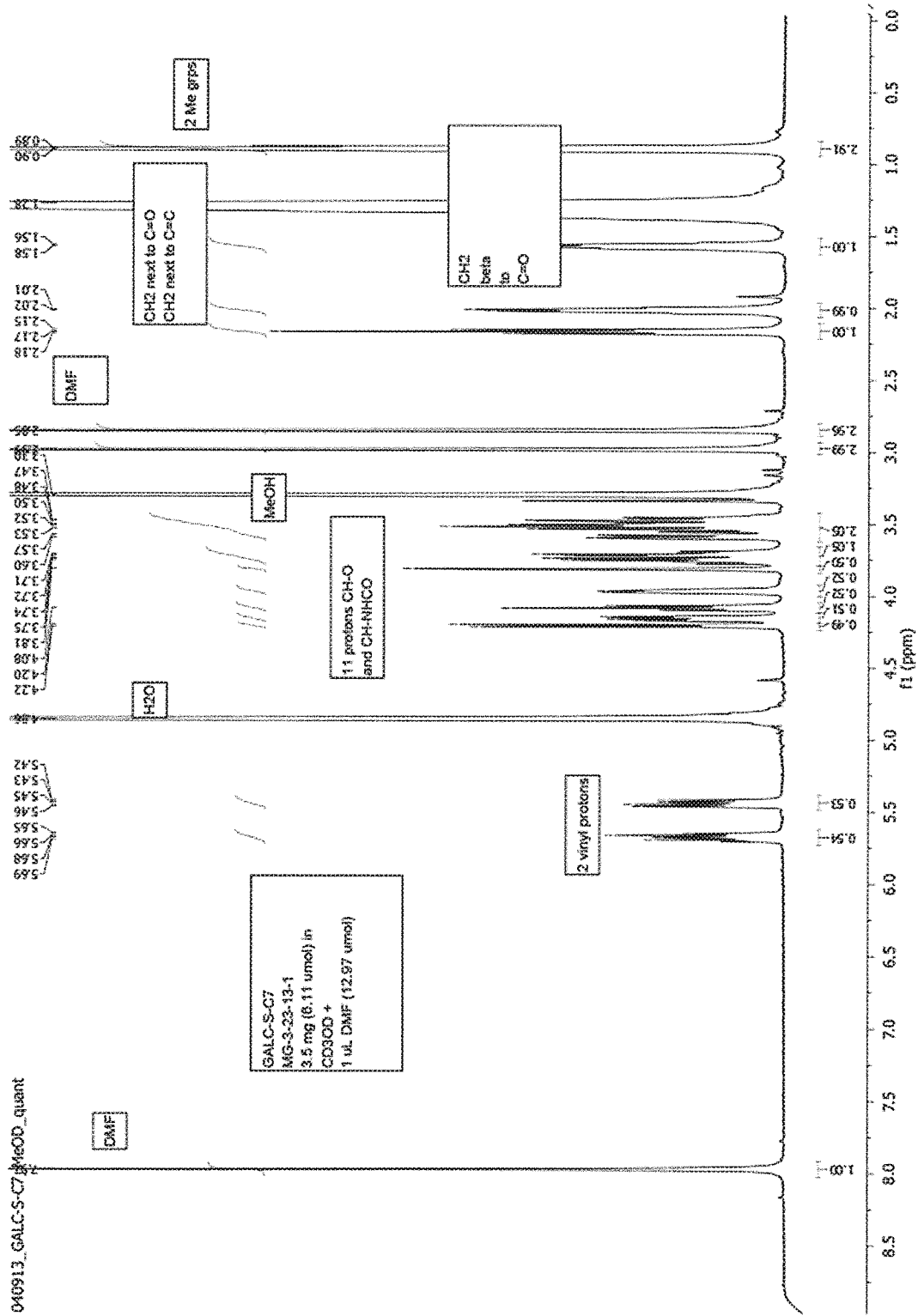
FIG. 1B illustrates NMR analysis of a second substrate according to one embodiment.

As one additional example, compound 7 was synthesized substantially as depicted in Scheme II:

Briefly, 100 mg of galactosyl-sphingosine (Avanti Polar Lipids, Inc., Alabaster, Ala.) was dissolved in 3.3 mL THF+0.56 mL water. To this solution 1.5 eq. of heptanoyl-NHS ester was added. The pH of the mixture was adjusted to 8.5-9.0 (spotting on water moistened pH paper) with diisopropylethylamine. The reaction is nearly complete within 2 hours as measured by TLC. To force the reaction to completion, another 0.75 eq. of heptanoyl-NHS ester is added, the pH adjusted as above, and the mixture stirred for total of 3-4 hrs at room temperature. The reaction product is subjected to centrifugation in a Speed-Vac overnight without heating. The dried reside was dissolved in 1.4 mL of DMF and 0.2 mL portions were injected onto the HPLC column as above. Product fractions were pooled from all of the HPLC runs, and solvent was removed in a centrifugal concentrator (Speed-Vac, oil pump vacuum, room temperature) to give the desired product in 81% yield. Compound synthesis is confirmed by NMR as illustrated in FIG. 1B.

Example 2

Preparation of Internal Standards

Internal standards are made by processes similar to those of Example 1 but beginning with sphingosine that is not bound to a sugar moiety substantially as illustrated in Scheme III.

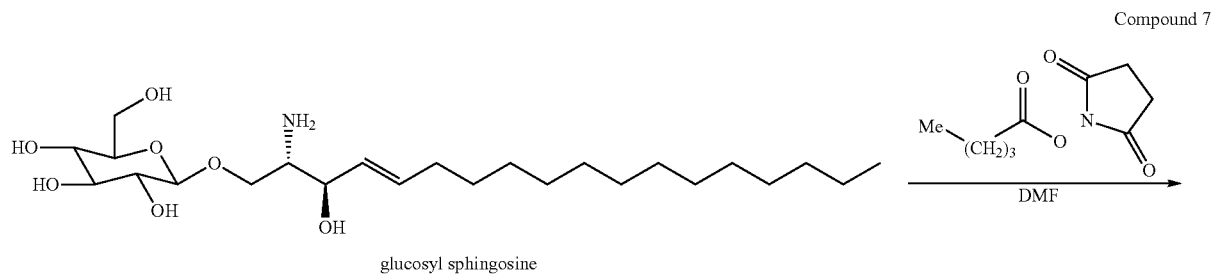

glucosyl sphingosine

Compound 7

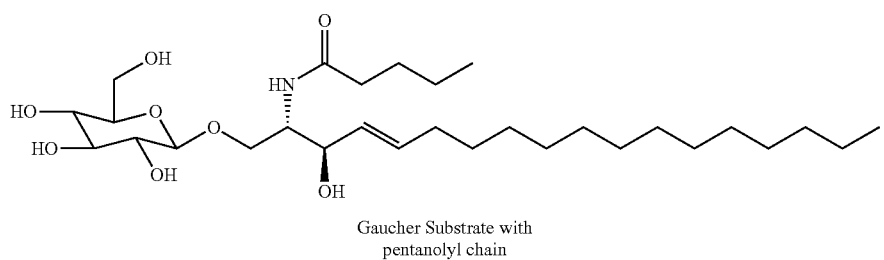

Gaucher Substrate with
pentanolyl chain

Scheme III

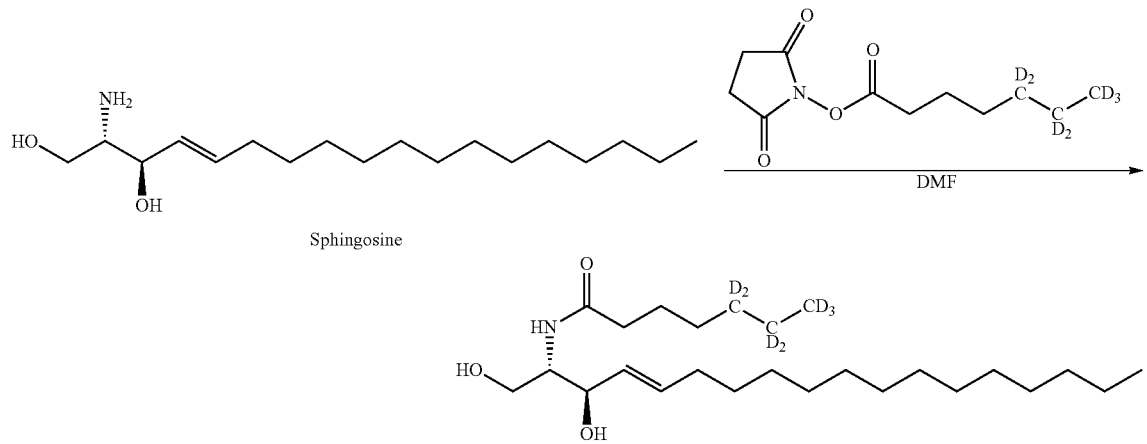

Briefly, commercially available sphingosine (Avanti Polar Lipids, Alabaster, Ala.) and the appropriate NHS ester of fatty acid are reacted as in Example 1. Example NHS esters used are: pentanoyl-NHS ester, heptanoyl-NHS ester, pentanoyl-NHS ester (each with or without H to D substitution). Internal standards are purified as above by HPLC and are obtained in yields of 20-90%.

Compound 81

The resulting exemplary Compound 81 is analyzed by NMR to confirm synthesis with a resulting molecular weight of 424. The process of Scheme II is similarly used to synthesize other labeled internal standards that include a H to D substitution in either the sphingosine or the NHS ester precursor. Additional exemplary compounds according to Formula V synthesized are presented in Table 2.

TABLE 2

| Compound | $R^1$ alkyl chain length | $R^2$ alkyl chain length | NHS ester | MW |
|---|---|---|---|---|
| 82* | $C_3$ | $C_{13}$ | butyroyl | |
| 83* | $C_4$ | $C_{13}$ | pentanoyl | 392.40 |
| 84* | $C_5$ | $C_{13}$ | hexanoyl | 408.42 |
| 85** | $C_6$ | $C_{13}$ | heptanoyl | |
| 86** | $C_6$ | $C_{13}$ | heptanoyl | |

*signifies that the NHS fatty acid includes H to D substitutions.
**signifies that the sphingosine includes terminal H to D substitutions.

Example 3

Detection Enzyme Activity in a Sample

The substrates of Compounds 1 and 7 are used to detect the presence of acid-β-glucocerebrosidase (ABG) and galactocerebroside-β-galactosidase (GALC) respectively. Blood is obtained by venipuncture from consenting adult humans and blotted on filter paper. For each sample, a disk of 3 mm diameter is punched from the areas of dried blood into a well of a 96-well microtiter plate. The blood disk is then incubated directly with an assay solution containing substrates at a final concentration of 500 μmol/L and corresponding internal standards at a final concentration of 5 μmol/L. To the assay solution, a final concentration of 0.5 mol/L sodium acetate buffer with sodium taurocholate is also added. The assay mixture containing the blood disk is incubated for 15 to 24 hours at 37° Celsius with orbital shaking (150 rpm) in a thermostatic air shaker. After the incubation period, an aliquot of pure methanol is added to each tube or well to terminate the enzymatic reaction. Before going into the mass spectrometer, the incubated reaction mixture is diluted with pure methanol. For the mass spectrometry analysis, the electrospray source is operated in positive mode, and the ions are detected in parent-ion scan mode. The amount of enzymatic product is calculated from the ion abundance ratio of the product to the internal standard minus that of a blank.

Figure 6:
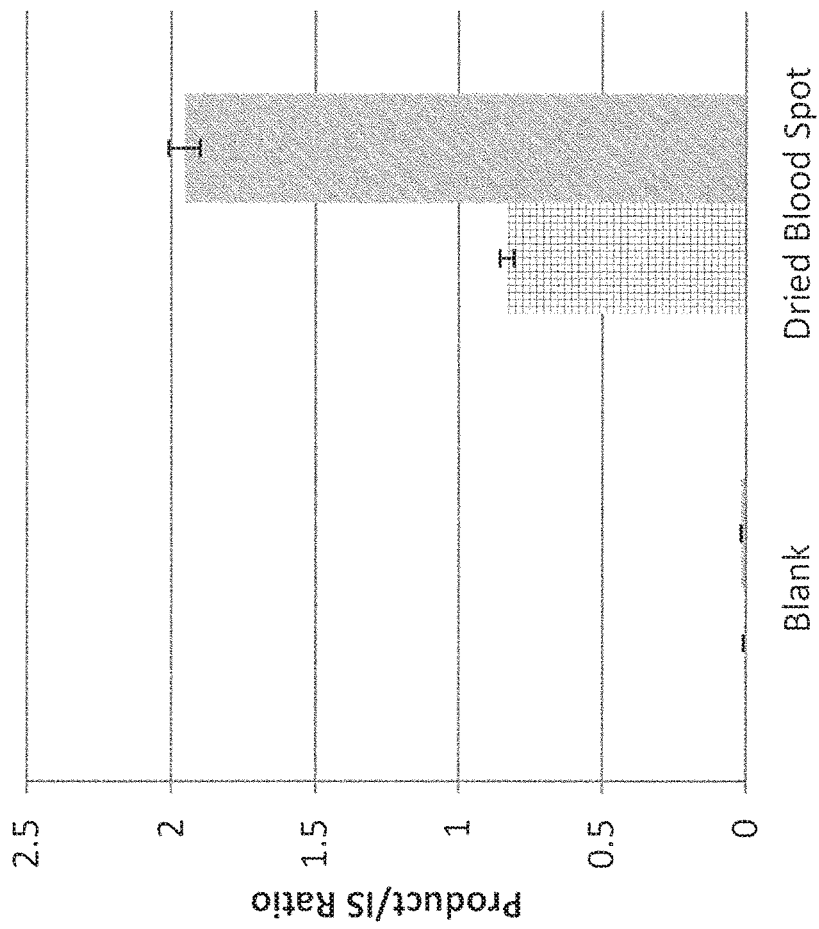
FIG. 6 is a graph of experimental results comparing the performance of substrates of the present invention (hashed) with the performance of prior art substrates (checked) in an analytical procedure for detecting lysosomal storage disorders.

FIG. 6 illustrates the unexpectedly improved results using compound 1 as the ABG substrate relative to previously used substrates illustrating a 2-fold improvement in product detection over a similar compound substituting the $C_5$ amido for a $C_{12}$ amido. Samples positive for GALC demonstrate a positive ion with molecular weight 264.27. The corresponding internal standard produces a positive ion with molecular weight 271.31.

Example 4

Simultaneous Detection of Multiple Enzyme Activity in a Sample

The substrates of Compounds 1 and 7 are used simultaneously to detect the presence of acid-β-glucocerebrosidase (ABG) and galactocerebroside-β-galactosidase (GALC) respectively. Blood is obtained by venipuncture from consenting adult humans and blotted on filter paper. For each sample, a disk of 3 mm diameter is punched from the areas of dried blood into a well of a 96-well microtiter plate. The blood disk is then incubated directly with an assay solution containing substrates at a final concentration of 100 μmol/L and corresponding internal standards at a final concentration of 1 μmol/L. To the assay solution, a final concentration of 0.5 mol/L sodium acetate with sodium taurocholate buffer is also added (30 μl final assay volume). The assay mixture containing the blood disk is incubated for 15 to 24 hours at 37° Celsius with orbital shaking (150 rpm) in a thermostatic air shaker. After the incubation period, a 100 μl aliquot of 50:50 methanol/ethyl acetate is added to each tube or well to terminate the enzymatic reaction. The reaction is then supplemented with 400 μl HPLC grade ethyl acetate and 200 μl water. The reaction is centrifuged and the resulting top layer of the liquid is transferred to a new assay plate and evaporated under nitrogen. An analysis buffer of 83% acetonitrile/17% water with 0.1% formic acid is added to the assay plate and the samples subjected to analysis by MS/MS to detect enzymatic products and internal standards. For mass spectrometry analysis, the electrospray source is operated in positive mode, and the ions are detected in parent-ion scan mode. The amount of enzymatic product is calculated from the ion abundance ratio of the product to the internal standard minus that of a blank. Detection of both ABG and GALC is achieved.

Example 5

In an alternative embodiment the product of the reaction with the substrates of Formula I is quantified by immunoassay. Blood spotted on filter paper is reconstituted in buffer to liberate the active components. One or an array of substrates is added to the reaction chamber and the reaction allowed to proceed overnight (~14 hours). The reaction is quenched by the addition of 6× volume glycine/NaOH pH 10.4. A sample of each reaction is added to the wells of a high-binding irradiated microtiter plate and incubated overnight to allow sufficient binding of the reaction product to the wells of the plate. A standard curve of product in similar buffer/sample is also added to the plate to serve as a basis for quantitation. After complete binding to the surface of the plate, the wells are washed twice with phosphate buffered saline (PBS) by the use of a squirt bottle, plate washer, or any other automated or non-automated plate washing system. Any additional sites for protein binding are subsequently blocked by the addition of a blocking agent illustratively including 3% bovine serum albumin in PBS or any other synthetic or natural blocking agent known in the art. The blocking agent is incubated for two hours at room temperature. The wells are washed 3× with PBS. The primary antibody(s) is then added to the wells to recognize and bind the remaining substrate, or the product. The antibody(s) is incubated in the wells for at least 2 hours. The plate is washed four times to remove unbound antibody. If the primary antibody is labeled the plate is used for detection. Optionally, a labeled secondary antibody is placed in the plate wells and allowed to incubate for an additional 2 hours followed by washing 4 times and detection by the appropriate method such as by a fluorescent or optical plate reader.

Example 6

In an alternative embodiment the product of the reaction with the substrates of Formula III is quantified by immunoassay. Blood spotted on filter paper is reconstituted in buffer to liberate the active components. One or an array of substrates immobilized to encoded particles is added to the reaction chamber, preferably a microplate well, and the reaction allowed to proceed overnight (~14 hours). A standard curve of enzyme in similar buffer/sample is also added to separate sets of encoded particles to serve as a basis for quantitation. The reaction is quenched by the addition of 6× volume glycine/NaOH pH 10.4. The primary antibody(s) is then added to the wells to recognize and bind the remaining substrate, or the product. The antibody(s) is incubated for at least 30 minutes. If the primary antibody is labeled the assay is ready for detection. Optionally, a labeled secondary antibody is placed in the plate wells and allowed to incubate for an additional 30 minutes. Detection is accomplished a flow cytometer.

Example 7

An active terminal amino group on the $B^2$ of an exemplary embodiment of Formula I or the $R^1$ or $R^2$ group of Formula II or III is amenable to numerous labeling procedures. In a representative example, the terminal amine is specifically labeled with fluoroisothiocyanate (FITC). Derivitization of the substrate is performed by addition of a FITC molecule to the terminal amine of the $B^2$ group. Similar modification may be performed on amine groups that are not on the terminal carbon, if present. The purified/lyophilized substrate is resuspended in 0.1 M sodium bicarbonate buffer, pH 9.0 at a concentration of 5 mg/ml. Immediately prior to reaction with substrate, dissolve 5 mg of FITC dye in 0.5 ml of DMSO in the dark. With gentle vortexing, add 0.1 ml of dye solution of the substrate solution and incubate for 1 hour at room temperature in the dark. The free unreacted dye is removed by gel filtration on a 10×300 mm Sephadex G column pre-equilibrated in phosphate buffered saline. Concentration of the final product is determined by mass spectrometry or other method known in the art. The labeled substrate is optionally concentrated and aliquotted for storage at −20° C. until further use.

The labeled substrate is used in a reaction for the detection of glucocerebrosidase activity and the detection of Gaucher's disease. For each patient or control sample, a disk of 3 mm diameter is punched from the areas of dried blood on a filter paper into a micro-centrifuge tube or a well of a 96-well microtiter plate. The blood disk is then incubated directly with an assay solution containing labeled substrate at a final concentration of 5 μmol/L and internal standards at a final concentration of 0.1 μmol/L. The assay mixture containing the blood disk is incubated for 15 to 24 hours at 37° C. with orbital shaking (150 rpm) in a thermostatic air shaker. After the incubation period, an aliquot of pure methanol is added to each tube or well to terminate the enzymatic reaction. A sample of the reaction is added to a second tube containing a HPLC mobile phase (methanol: water:acetic acid, 82:18:0.1 vol/vol/vol). A 20-μl aliquot of the quenched reaction solution is separated on a 4.6×250-mm Symmetry $C_{18}$ reverse-phase HPLC column (Waters, Milford, Mass.) isocratically, at a rate of 1.3 ml/min using methanol:water:acetic acid at 82:18:0.1 vol/vol/vol as a mobile phase. Fluorescence intensity is continuously monitored using a fluorescence detector (model L-7480; Hitachi, Naperville, Ill.) at a medium gain sensitivity. The amount of labeled product in the sample is determined by comparing the area of the peak to that of an external standard comprised of labeled product at a known concentration. The concentration of product in the reaction is readily determined and the activity of glucocerebrosidase determined by dividing the moles product/per unit of reaction time.

Any patents or publications mentioned in this specification are indicative of the levels of those skilled in the art to which the invention pertains. These patents and publications are herein incorporated by reference to the same extent as if each individual publication was specifically and individually indicated to be completely incorporated by reference.

One skilled in the art will readily appreciate that the present invention is well-adapted to carry out the objects and obtain the ends and advantages mentioned, as well as those inherent therein. The present examples along with the methods, procedures, treatments, molecules and specific compounds described herein are presently representative of specific embodiments, are exemplary, and are not intended as limitations on the scope of the invention. It will be apparent that other embodiments exist and are encompassed within the spirit of the invention as defined by the scope of the claims.

The invention claimed is:

1. A method for detecting enzymatic activity, comprising:
contacting a sample containing a target enzyme with a composition comprising a first substrate and a second substrate, under conditions wherein the target enzyme is capable of acting on the first substrate or the second substrate to produce an enzymatic product; and
detecting said enzymatic product;
the first substrate having the formula:

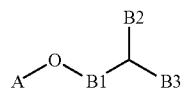

where A is a galactose linked to O by a glycosidic bond;
B1 is selected from the group consisting of: a $C_1$-$C_{20}$ alkyl; a heteroatom containing $C_1$-$C_{20}$ alkyl; $C_2$-$C_{20}$ alkenyl; a heteroatom containing $C_2$-$C_{20}$ alkenyl; and a substituted or unsubstituted $C_6$-$C_{20}$ aryl;
B2 is selected from the group consisting of: a $C_2$-$C_7$ urethane; a $C_2$-$C_7$ amido; a $C_2$-$C_7$ ester; a $C_2$-$C_7$ uriedo; a $C_2$-$C_7$ carbamato; a $C_2$-$C_7$ carbonyl; a $C_1$-$C_7$ alkyl; a heteroatom containing $C_1$-$C_7$ alkyl; a $C_1$-$C_7$ alkyl having a substituent of N, O, or S; a $C_2$-$C_7$ alkenyl; a heteroatom containing $C_2$-$C_7$ alkenyl; and a $C_2$-$C_7$ alkenyl having a substituent of N, O, or S; and
B3 is selected from the group consisting of: a $C_1$-$C_{20}$ alkyl; a heteroatom containing $C_1$-$C_{20}$ alkyl; $C_1$-$C_{20}$ alkyl having a substituent of N, O, or S; $C_4$-$C_{20}$ ether; $C_1$-$C_{20}$ ester; $C_1$-$C_{20}$ alkenyl; a heteroatom containing $C_1$-$C_{20}$ alkenyl; $C_2$-$C_{20}$ alkenyl having a substituent of N, O, or S; $C_1$-$C_{20}$ alkynl; a heteroatom containing $C_1$-$C_{20}$ alkynl; $C_2$-$C_{20}$ alkynl having a substituent of N, O, or S; $C_6$-$C_{20}$ aryl; and a $C_6$-$C_{20}$ heterocyclic containing a heteroatom of N, O or S; and
the second substrate having the formula:

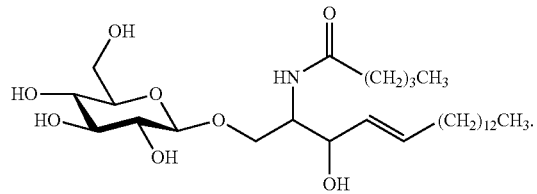

2. The method of claim 1 wherein said target enzyme is acid galactocerebroside β-galactosidase or acid-β-glucocerebrosidase and said wherein said B2 is a $C_2$-$C_7$ amido, and B3 is a $C_{13}$-$C_{20}$ having a substituent of O present as a hydroxyl.
3. The method of claim 1 wherein A is a a D-galactose.
4. The method of claim 1 wherein B1 is a methylene.
5. The method of claim 1 where B2 is a $C_2$-$C_7$ amido.
6. The method of claim 1 wherein B3 is a $C_2$-$C_{20}$ alkenyl having a substituent of N, O, or S.
7. The method of claim 1 wherein: A is a D-galactose; B1 is a $C_1$-$C_2$ alkyl or a $C_6$ aryl; and B2 is a $C_2$-$C_7$ amido.
8. The method of claim 7 wherein B3 is a $C_2$-$C_{20}$ alkenyl having a substituent of N, O, or S.
9. The method of claim 1 wherein the first substrate comprises:

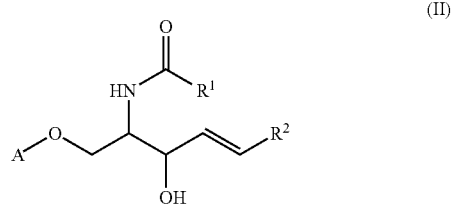

where: A is galactose; $R^1$ is a $C_1$-$C_6$ alkyl or a $C_2$-$C_6$ alkenyl; and $R^2$ is a $C_1$-$C_{20}$ alkyl, a $C_1$-$C_{20}$ alkyl having a substituent of N, O, or S, a $C_1$-$C_{20}$ alkenyl, or a $C_1$-$C_{20}$ alkenyl having a substituent of N, O or S.
10. The method of claim 9 wherein A is a D-galactose, $R^1$ is a $C_4$-$C_6$ alkyl, and $R^2$ is a $C_{13}$-$C_{20}$ alkyl, a $C_{13}$-$C_{20}$ alkyl having a substituent of N, O, or S, a $C_{13}$-$C_{20}$ alkenyl, or a $C_{13}$-$C_{20}$ alkenyl having a substituent of N, O or S.
11. The method of claim 9 wherein $R^2$ is a $C_{13}$ alkyl.

* * * * *